(12) United States Patent
Simpkins

(10) Patent No.: US 9,387,162 B2
(45) Date of Patent: Jul. 12, 2016

(54) METHODS AND COMPOSITIONS FOR TREATING CONDITIONS RELATED TO LACK OF BLOOD SUPPLY, SHOCK, AND NEURONAL INJURIES

(71) Applicant: Cuthbert O. Simpkins, Shreveport, LA (US)

(72) Inventor: Cuthbert O. Simpkins, Shreveport, LA (US)

(73) Assignee: VIVACELLE BIO, INC., Shreveport, LA (US)

( * ) Notice: Subject to any disclaimer, the term of this patent is extended or adjusted under 35 U.S.C. 154(b) by 246 days.

(21) Appl. No.: 14/086,492

(22) Filed: Nov. 21, 2013

(65) Prior Publication Data

US 2014/0112961 A1 Apr. 24, 2014

Related U.S. Application Data

(63) Continuation of application No. 13/273,471, filed on Oct. 14, 2011, now Pat. No. 8,618,056, which is a continuation-in-part of application No. 12/314,737, filed on Dec. 16, 2008, now Pat. No. 8,063,020, which is a continuation-in-part of application No. 12/696,107, filed on Jan. 29, 2010, now abandoned.

(60) Provisional application No. 61/016,443, filed on Dec. 22, 2007, provisional application No. 61/064,639, filed on Mar. 18, 2008, provisional application No. 61/202,124, filed on Jan. 30, 2009, provisional application No. 61/490,816, filed on May 27, 2011, provisional application No. 61/432,919, filed on Jan. 14, 2011.

(51) Int. Cl.
| | |
|---|---|
| A61K 8/00 | (2006.01) |
| A61K 9/00 | (2006.01) |
| A23L 1/035 | (2006.01) |
| A23L 1/30 | (2006.01) |
| A23L 1/305 | (2006.01) |
| A61K 9/107 | (2006.01) |
| A61K 31/4172 | (2006.01) |
| A61K 31/66 | (2006.01) |
| A61K 38/33 | (2006.01) |
| A61K 45/06 | (2006.01) |
| A61K 47/10 | (2006.01) |

(52) U.S. Cl.
CPC ............ *A61K 9/0026* (2013.01); *A23L 1/035* (2013.01); *A23L 1/3006* (2013.01); *A23L 1/3051* (2013.01); *A61K 9/0019* (2013.01); *A61K 9/107* (2013.01); *A61K 31/4172* (2013.01); *A61K 31/66* (2013.01); *A61K 38/33* (2013.01); *A61K 45/06* (2013.01); *A61K 47/10* (2013.01)

(58) Field of Classification Search
CPC .................................................. A61K 8/062

IPC ....................................................... A61K 8/062
See application file for complete search history.

(56) References Cited

U.S. PATENT DOCUMENTS

| | | | |
|---|---|---|---|
| 4,182,750 A | 1/1980 | Sullivan et al. | |
| 4,330,557 A | 5/1982 | Cavazza | |
| 4,425,334 A | 1/1984 | Hunt | |
| 4,618,621 A | 10/1986 | Tang | |
| 4,895,876 A | 1/1990 | Schweighardt et al. | |
| 4,911,929 A | 3/1990 | Farmer et al. | |
| 5,284,663 A | 2/1994 | Speaker | |
| 5,374,624 A | 12/1994 | Segel | |
| 5,438,041 A | 8/1995 | Zheng et al. | |
| 5,576,016 A | 11/1996 | Amselem et al. | |
| 5,635,207 A | 6/1997 | Grinstaff et al. | |
| 5,726,209 A | 3/1998 | Flaim et al. | |
| 5,846,516 A | 12/1998 | Riess et al. | |
| 6,261,537 B1 | 7/2001 | Klaveness et al. | |
| 7,105,151 B2 | 9/2006 | Unger et al. | |
| 7,261,903 B1 | 8/2007 | Weinberg et al. | |
| 7,417,118 B2 | 8/2008 | Kai et al. | |
| 2001/0028893 A1 | 10/2001 | Spears | |
| 2002/0172710 A1 | 11/2002 | Twine | |
| 2002/0183394 A1* | 12/2002 | Gupta | A61K 9/1075 514/613 |
| 2003/0113351 A1 | 6/2003 | Fischer et al. | |
| 2005/0260189 A1 | 11/2005 | Klibanov et al. | |
| 2006/0008480 A1* | 1/2006 | Chen | A61K 9/0019 424/400 |
| 2006/0088583 A1 | 4/2006 | Takeoka et al. | |
| 2006/0166182 A1 | 7/2006 | Weinberg et al. | |
| 2007/0149617 A1 | 6/2007 | Deckelbaum et al. | |
| 2008/0275371 A1 | 11/2008 | Hoffmann | |
| 2009/0163418 A1 | 6/2009 | Simpkins | |

(Continued)

FOREIGN PATENT DOCUMENTS

| | | |
|---|---|---|
| WO | 03009828 | 2/2003 |
| WO | 2004060147 | 7/2004 |
| WO | 2009082449 | 7/2009 |

OTHER PUBLICATIONS

Extended European Search Report issued on Jun. 6, 2014, in corresponding European Patent Application No. 11855887.
International Preliminary Report and Written Opinion of the International Searching Authority issued in International Application No. PCT/US2011/056288, mailed on Jul. 25, 2013.
International Search Report issued in International Patent Application No. PCT/US2010/000262, mailed on Jan. 20, 2011.
Supplemental European Search Report issued in European Patent Application No. 08 86 5306, mailed on Jan. 28, 2011.

(Continued)

*Primary Examiner* — Ruth Davis
(74) *Attorney, Agent, or Firm* — Michael Ye; Andrews Kurth LLP

(57) ABSTRACT

A pharmaceutical composition comprising a lipid component; an amphiphilic emulsifier; and a polar liquid carrier. The lipid component and the amphiphilic emulsifier form free-moving lipid-carrying micelles (LMs) in the polar liquid carrier. The pharmaceutical composition is free of hemoglobin and fluorocarbon and can be used for treating conditions related to lack of blood supply and to raise the blood pressure.

34 Claims, 3 Drawing Sheets

(56) References Cited

U.S. PATENT DOCUMENTS

| | | |
|---|---|---|
| 2009/0191244 A1 | 7/2009 | Kheir et al. |
| 2010/0178347 A1 | 7/2010 | Bullock et al. |
| 2010/0196461 A1 | 8/2010 | Simpkins |
| 2010/0256083 A1 | 10/2010 | Dobson |

OTHER PUBLICATIONS

Yun Suk Jo, et al., "Micelles for Delivery of Nitric Oxide", JACS Articles J. Am. Chem. Soc., 2009, 131 pp. 14413-14418.
Evan C. Under, et al., "Therapeutic applications of the lipid-coated microbubbles", Advanced Drug Delivery Reviews, 56, 2004, pp. 1291-1314.
Meg A. Rosenblatt, et al., "Successful Use of a 20% Lipid Emulsion to Resuscitate a Patient after a Presumed . . . ", Anesthesiology, vol. 105, No. 1, Jul. 2006, pp. 217-221.
J. Eckart, et al., "Aktueller Stand der Parenteralen Ernahrung mit Fettemulsionen", Infusionstherapic, 10, 1983, pp. 172-182.
G. Foxall, et al., "Levobupivacaine-induced seizures and cardiovascular collapse treated with Intralipid", The Ass. of Anaesthesia . . . ,62, 2007, pp. 516-518.
Susan Lanza-Jacoby, Ph.D., et al., "Parenteral Supplemental With a Fish-Oil emulsion Prolong Survival and Improves Rat Lymphocyte . . . ", Nutrition, 17, 2001, pp. 112-116.
R.J. Litz, et al., "Successful resuscitation of patient with ropivacaine-induced asystole after auxiliary plexus block . . . ", The Ass. of Anaesthesia, 2006, 61, pp. 800-801.
International Search Report issued in International Application No. PCT/US2008/013781, mailed on Aug. 7, 2009.
Robert J. Przybelski, M.D., et al., "Advances in Blood Substitutes; Industrial Opportunities and Medical Challenges", Chapter 5, pp. 71-85.
Cuthbert O. Simpkins, et al., "Histidine Inhibits the Degradation of Cells Suspended in Ringer's Lactrate", The Journal of Trauma, 2007, pp. 565-572.
European Search Report issued in European Patent Application No. 10736154.5-2123, mailed on Apr. 10, 2012.
Cuthbert O. Simpkins, et al., "Abstract P112: Vivasure: An Oxygen-Carrying Lipid Emulsion for Resuscitation", Circulation, Nov. 3, 2009, vol. 18, No. Suppl. 2.
File History of U.S. Appl. No. 13/273,471, filed Oct. 14, 2011.
File History of U.S. Appl. No. 12/696,107, filed Jan. 29, 2010.
File History of U.S. Appl. No. 12/314,737, filed Dec. 16, 2008.
File History of U.S. Appl. No. 60/975,705, filed Sep. 27, 2007.
File History of U.S.Appl. No. 61/026,984, filed Feb. 7, 2008.
Battino, et al., "The Solubilities of Seven Gases in Olive Oil with Reference to Theories of Transport Through the Cell Membrane," Department of Chemistry, Wright State University, Dayton, Ohio, 45431, pp. 830-833, Dec. 1968.
Simpkins, et al., "Naloxene Inhibits Superoxide Release from Human Neutrophils," Life Sciences, vol. 37, pp. 1381-1386, 1985.
Franks, et al., "Halothane, Isoflurane, Xenon, and Nitrous Oxide Inhibit Calcium ATPase Pump Activity in Rat Brain Synaptic Plasma Membranes," Anesthesiology, 82, pp. 108-117, 1995.
Heimburg, et al., "The Thermodynamics of General Anesthesia," Biophysics Journal, vol. 92, May 2007, pp. 3159-3165.
Ma, et al., "Neuroprotective and neurotoxic properties of the 'inert' gas, xenon," British Journal of Anaesthesia 89 (5), pp. 739-746, 2002.
Loetscher, et al., "Argon: Neuroprotection in in vitro models of cerebral ischemia and traumatic brain injury," Critical Care, 13, R206, 2009 (doi: 10.1186/ccf8214), http://ccforum.com/content/13/6/R206.
Baumert, et al., "Xenon anaesthesia may preserve cardiovascular function in patients with heart failure," Acta Anaesthesiol. Scand. 49, pp. 743-749, 2005.
Grimley, et al, "Quantitiation of dissolved gas content in emulsions and in blood using mass spectrometric detection," Journal of Chromatography B, 879, pp. 1513-1518, 2011.

* cited by examiner

METHODS AND COMPOSITIONS FOR TREATING CONDITIONS RELATED TO LACK OF BLOOD SUPPLY, SHOCK, AND NEURONAL INJURIES

RELATED APPLICATIONS

This application is a continuation of U.S. application Ser. No. 13/273,471, filed on Oct. 14, 2011, now allowed, which is a continuation-in-part of U.S. application Ser. No. 12/314,737, filed on Dec. 16, 2008, now U.S. Pat. No. 8,063,020, which claims the priority of U.S. Provisional Application No. 61/016,443, filed on Dec. 22, 2007 and U.S. Provisional Application No. 61/064,639, filed on Mar. 18, 2008; U.S. application Ser. No. 13/273,471 is also a continuation-in-part of U.S. application Ser. No. 12/696,107, filed on Jan. 29, 2010, which claims priority of U.S. Provisional Application Ser. No. 61/202,124 filed Jan. 30, 2009; U.S. application Ser. No. 13/273,471 also claims priority of U.S. Provisional Application No. 61/432,919, filed on Jan. 14, 2011 and U.S. Provisional Application No. 61/490,816, filed on May 27, 2011. All of the aforementioned applications are incorporated herein by reference in their entirety.

FIELD

The technical field is medical treatment and, in particular, methods and compositions for treating conditions related to lack of blood supply, shock and neuronal injuries.

BACKGROUND

Shock is a consequence of inadequate circulation due to causes that include blood loss, vasodilation or dehydration. The loss of circulation deprives cells of oxygen and nutrients and activates a powerful inflammatory response. Such states occur after injury due to war, accident, and assault resulting in massive blood loss or due to massive infection. The current therapeutic approach is to rapidly infuse fluids in order to restore circulating volume. This rapid infusion of fluids may be combined with pharmacological agents that directly constrict blood vessels. Both the infusion of fluids and the administration of drugs that constrict blood vessels cause an increase in the blood pressure. However, the pathophysiology of shock is far more complex than that which can be remedied by simply adding volume and clamping down the blood vessels to create a higher blood pressure. Once shock has occurred and the longer it persists numerous toxic substances termed mediators are released into the blood stream. These mediators create a dangerous state that is markedly different from that which existed prior to the event that led to shock.

Current methods for treating shock are of limited efficacy. Examples of resuscitation fluids are either crystalloids that contain various salts such as Ringer's lactate that rapidly diffuses out of the bloodstream and those that contain colloids or large molecules that remain in the bloodstream a longer time such as those that contain Hetastarch, a plasma volume expander derived from natural sources of starch. Numerous complications have been observed with both. Hetastarch enhances bleeding, a counterproductive property after massive blood loss. Overreliance on vasoconstrictors will raise the blood pressure but decrease tissue perfusion leading to tissue necrosis and death.

Therefore, there exists a need for a low-cost therapeutic volume expander that is capable of bringing oxygen and nutrients to the tissue and reduce inflammatory responses.

SUMMARY

One aspect of the present invention relates to a pharmaceutical composition comprising a lipid component, an amphiphilic emulsifier, and a polar liquid carrier. The lipid component and the amphiphilic emulsifier form free-moving lipid-carrying micelles (LMs) in the polar liquid carrier. The pharmaceutical composition is free of hemoglobin and fluorocarbon.

Another aspect of the present invention relates to a pharmaceutical composition comprising 10%-80% (w/v) of a lipid component selected from the group consisting of soybean oil, chia bean oil and algae oil; 1%-5% (w/v) of an amphiphilic emulsifier selected from the group consisting of egg yolk phospholipids and α-phosphatidylcholine; 2%-5% (w/v) glycerol or mannitol; 5% (w/v) albumin; 0.1 fM-10 mM histidine or cysteine; and a polar liquid carrier, wherein the lipid component and the amphiphilic emulsifier form free-moving lipid-carrying micelles (LMs) in the polar liquid carrier, wherein said LMs have an average diameter of 100 to 500 nm and wherein the pharmaceutical composition is free of hemoglobin and fluorocarbon.

Another aspect of the present invention relates to a method for raising blood pressure in a shock patent. The method comprises the step of infusing into said patient, an effective amount of a pharmaceutical composition comprising a lipid component; an amphiphilic emulsifier; and a polar liquid carrier, wherein the lipid component and the amphiphilic emulsifier form free-moving lipid-carrying micelles (LM) in the polar liquid carrier, wherein the pharmaceutical composition is free of hemoglobin and fluorocarbon, and wherein the pharmaceutical composition is infused in an amount that equals to, or is greater than, 10% of the normal blood volume of the shock patient at a rate greater than 200 ml/min.

Another aspect of the present invention relates to a method for treating a shock patent. The method comprises (a) infusing into said patient, an effective amount of a first pharmaceutical composition comprising: a first lipid component comprising soy bean oil; a first amphiphilic emulsifier; and a first polar liquid carrier, wherein the first lipid component and the first amphiphilic emulsifier form free-moving lipid-carrying micelles (LM) in the first polar liquid carrier, wherein the first pharmaceutical composition is free of hemoglobin and fluorocarbon; and (b) infusing into said patient, an effective amount of a second pharmaceutical composition comprising: a second lipid component comprising chia bean oil; a second amphiphilic emulsifier; and a second polar liquid carrier, wherein the second lipid component and the second amphiphilic emulsifier form free-moving LMs in the second polar liquid carrier, wherein the second pharmaceutical composition is free of hemoglobin and fluorocarbon.

BRIEF DESCRIPTION OF THE DRAWINGS

The detailed description will refer to the following drawings, wherein like numerals refer to like elements, and wherein.

DETAILED DESCRIPTION

One aspect of the present invention relates to a pharmaceutical composition for treating conditions related to lack of blood supply with a pharmaceutical composition. The pharmaceutical composition comprises a lipophilic component, an emulsifier and a polar liquid carrier. The lipophilic component is dispersed in the polar liquid carrier to form an emulsion that typically contains single layer micelles with a polar outer surface and an inner hydrophobic space filled with the lipophilic component and/or other hydrophobic molecules. In certain embodiments, liposomes comprised of a lipid bilayer may also be employed. The pharmaceutical composition can be used to increase blood pressure and to carry oxygen to tissues in the absence of natural or modified hemoglobin. The pharmaceutical composition is free of hemoglobin, derivatives of hemoglobin, perfluorocarbon and derivatives of perfluorocarbon.

As used herein, a composition is "free of hemoglobin, derivatives of hemoglobin, perfluorocarbon and derivatives of perfluorocarbon" if the composition does not contain any hemoglobin, derivatives of hemoglobin, perfluorocarbon and derivatives of perfluorocarbon, or if the composition contains hemoglobin, derivatives of hemoglobin, perfluorocarbon and derivatives of perfluorocarbon at levels below 0.1% w/w.

Figure 1:
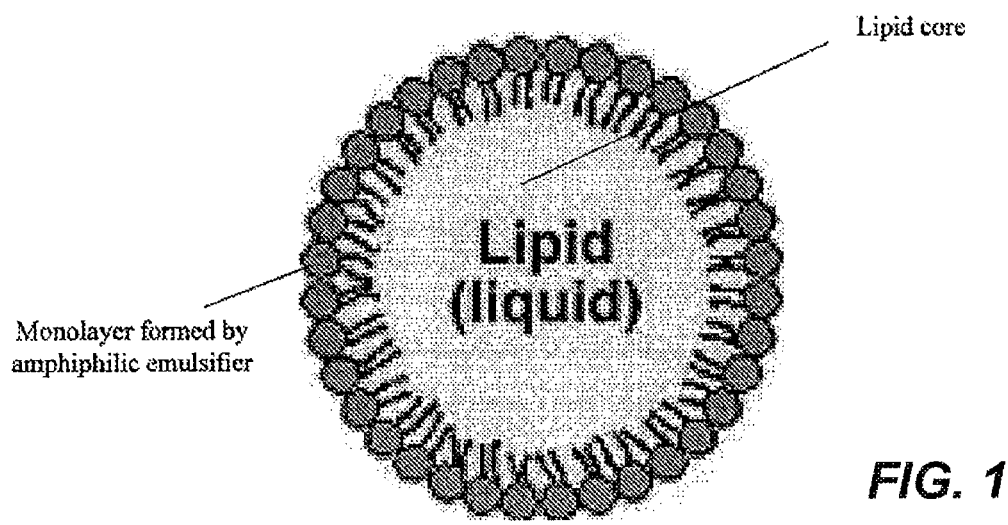
FIG. 1 is an illustration of a micelle containing a lipophilic core (yellow) and encapsulated by an emulsifier which may be a phospholipid or another amphiphilic molecule (mauve head black tails). The polar liquid carrier surrounds the micelle. These components together create an emulsion. The polar liquid may be water. This emulsion may be formed by adding energy to the mixture by sonication, using a homogenizer or a microfluidizer.

As shown in FIG. 1, the lipid component and the emulsifier form lipid-containing micelles (LM) that are surrounded by the polar carrier fluid (shown as the white space around the amphiphilic molecules). The amphiphilic emulsifier molecules occupy the periphery of the lipid boundary. The lipophilic ends of the amphiphilic emulsifier molecules are directed inward toward the lipid and the polar ends of the amphiphilic emulsifier molecules are directed outward toward the polar carrier fluid. Because hydrophobic gases, such as oxygen, preferentially dissolve in the lipid core of the micelles relative to water or other aqueous environments, the pharmaceutical composition of the present invention provides the ability to carry oxygen or other hydrophobic gases to body tissue. Emulsion comprised of the LM of the present invention is able to reverse the hypotension characteristic of hemorrhagic shock, and absorb and release lipophilic gases such as oxygen and nitric oxide. The LMs in the pharmaceutical composition are also capable of exerting an osmotic force and absorbing mediators of vascular patency, such as prostaglandins, nitric oxide, leukotrienes, and hromboxane, and other lipophilic mediators such as platelet activating factors.

In certain embodiments, the LM have diameters in the range of 10 to 5000 nm. The colloidal properties of the LM with a diameter range from 10 to 5000 nm promotes their retention in the intravascular space. In other embodiments, the LM have diameters in the range of 100 to 500 nm. In yet other embodiments, the LM have diameters that are less than 100 nm (nanoemulsions). In shock of any etiology in which the capillary permeability is increased, nanoemulsions would more readily get into the interstitial space than larger structures. In certain embodiments, the nanoemulsion comprises a mixture of micelles of 2-300 nm in diameter. In another embodiment, the nanoemulsion comprises micelles with an average diameter of about 1-30 nanometers (nano-micelles). At this size the micelle are able to get past the endothelial cell layer and enter the interstitial space. The nano-micelles may be employed in situations where the permeability of the vascular space has not increased or to promote cellular absorption of lipophilic mediators or to promote entry of molecules or cellular components that can favorably modulate intracellular mechanisms. Such modulatory effects may also be effected in the interstitial space especially in cases of increased vascular wall permeability. For example, one of the mechanisms of shock from hemorrhage or sepsis is the capillary leak. This capillary leak is caused by the death of endothelial cells and the actions of neitrophils. It is mediated by cytokines such as IL-1 and TNF as well as nitric oxide. Neutrophils adhere to damaged endothelial cells and release reactive oxygen species and cell wall damaging enzymes such as myeloperoxidase. The nano-micelles could get into the interstitium via the capillary leak and provide an anti inflammatory effect within the interstitial space.

In some embodiments, the pharmaceutical composition comprises a mixture of large micelles with diameters in the range of 100-400 nm and nano-micelles with diameters in the range of 1-30 nm. The larger micelles would tend to stay in the intravascular space and maintain intravascular volume while the nano-micelles could get into the interstitium where they could favorably affect survival by blocking reactive oxygen species and delivering salutary molecules, such as inhibitors of apoptosis (e.g., Z-VAD-FMY, an apoptosis inhibiting peptide) or protectors of mitochondrial integrity (e.g., Cyclosporin A, an inhibitor of mitochondrial inner pore opening). The nano-micelles may also be loaded with modulators of signal transduction such as diacylglycerol or cyclic GMP, or antioxidant such as Coenzyme Q10. In certain embodiments, the large micelles make up 10-40% (w/w) of the pharmaceutical composition, while the nano-micelles make up 5-30% (w/w) of the pharmaceutical composition. In other embodiments, the large micelles (100-400 nm) are made of soybean oil and the nano-micelles (1-30 nm) are made of chia bean oil, which has a grater anti inflammatory effect than that of soybean oil.

The solubility of hydrophobic gases in the lipophilic core promotes the uptake and transport of these gases to tissues. The endogenously produced gases carbon monoxide, nitric oxide and hydrogen sulfide can also be carried in the emulsion for the modulation of the vascular tone and apoptotic processes. Oxygen may also be loaded for delivery to tissues and the enhancement of aerobic metabolism. Xenon and argon are hydrophobic gases that could provide protection of the brain in hemorrhagic shock and in other pathological states such as seizures. Delivery of these gases to the brain may also provide pain relief.

In certain embodiments, the micelles in the pharmaceutical composition of the present invention are free-moving micelles that are not encapsulated in any type of particles. Further, the wall of the micelles is comprised of either a single layer or a double layer of the amphiphilic emulsifier molecules so that the micelles may easily merge with the cell membrane of the tissue that comes in contact with the pharmaceutical composition. Further, the micelles in the pharmaceutical composition of the present invention are free of hemoglobin, derivatives of hemoglobin, perfluorocarbon and derivatives of perfluorocarbon.

The conditions related to lack of blood supply include, but are not limited to, hypovolemia caused by bleeding, dehydration, vomiting, severe burns, systemic inflammatory response syndrome (SIRS) and drugs such as diuretics or vasodilators. Severe hypovolemia may occur in conjunction with capillary leak (CL), which is present in different conditions such as multiorgan dysfunction (MODS), sepsis, trauma, burn, hemorrhagic shock, post-cardiopulmonary bypass, pancreatitis and systemic capillary leak syndrome, and causes morbidity and mortality among a large number of hospital patients.

Lipophilic Component

The lipophilic component can be any pharmaceutically acceptable lipophilic material, such as lipids. As shown in FIG. 1 the lipophilic component is carried in the hydrophobic core of a micelle. The hydrophobic core may also consist of additives that may enhance the uptake of hydrophobic gases such as branched molecules an example of which is tri-n-octyl amine. In other embodiments, the lipophilic component is trapped in the forms of structures, such as erythrocyte ghosts.

As used herein, the term "lipid" refers to a fat-soluble material that is naturally occurring, or non-naturally occurring. Examples of lipids include but are not limited to, fatty acyls, glycerolipids, phospholipids, sphingolipids, sterol lipids, prenol lipids, saccharolipids, polyketides, non-natural lipid(s), cationic lipid(s), amphipathic alkyl amino acid derivative, adialkyldimethylammonium, polyglycerol alkyl ethers, polyoxyethylene alkyl ethers, tri-n-octylamine, boric acid, tris(3,5-dimethyl-4-heptyl)ester, triglycerides, diglycerides and other acylglycerols, such as tetraglycerol, pentaglycerol, hexaglycerol, heptaglycerol, octoglycerol, nonaglyceol and decaglycerol, and mixtures thereof. In certain embodiments, the lipophilic component comprises soybean oil, chia bean oil or algae oil.

In one embodiment, the lipophilic component is soybean oil. The lipophilic component may also be derived from chia beans that have a high concentration of anti-inflammatory omega 3 fatty acids. Soybean oil is thrombogenic and procoagulant, and therefore would be preferred for the initial phase of hemorrhagic shock when clotting is desired. After bleeding is no longer an issue, oils rich in omega 3 fatty acids would be favored because of their anti-thromobogenic properties. Oils rich in omega 3 fatty acids include, but are not limited to chia oil, algae oil, pumpkin oil, flaxseed oil or fish oil.

In certain embodiments, the lipid component comprises an unsaturated fatty acid with one or more alkenyl functional groups in cis or trans configuration. A cis configuration means that adjacent hydrogen atoms or other groups are on the same side of the double bond. In a trans configuration theses moieties are on different sides of the double bond. The rigidity of the double bond freezes its conformation and, in the case of the cis isomer, causes the chain to bend and restricts the conformational freedom of the fatty acid. In general, the more double bonds the chain has, the less flexibility it has. When a chain has many cis bonds, it becomes quite curved in its most accessible conformations. For example, oleic acid, with one double bond, has a "kink" in it, while linoleic acid, with two double bonds, has a more pronounced bend. Alpha-linolenic acid, with three double bonds, favors a hooked shape. The effect of this is that in restricted environments, such as when fatty acids are part of a phospholipid in a lipid bilayer, or triglycerides in lipid droplets, cis bonds limit the ability of fatty acids to be closely packed and therefore could affect the melting temperature of the membrane or of the fat. In some embodiments, the lipid component comprises up to 1%, 2%, 5%, 10%, 15%, 20%, 25%, 30%, 35%, 40%, 45%, 50%, 55%, 60%, 65%, 70%, 75%, 80%, 85%, 90%, 95% or 99% (w/w) unsaturated fatty acid(s) that have one or more alkenyl functional groups in cis configuration.

Examples of cis-unsaturated fatty acids include, but are not limited to, obtusilic acid, linderic acid, tsuzuic acid, palmitoleic acid, oleic acid, elaidic acid, vaccenic acid, petroselinic acid, gadoleic acid, eicosenoic acid, erucic acid, cetoleic acid, nervonic acid, ximenic acid and lumepueic acid; n-3 type unsaturated fatty acids such as α-linolenic acid, stearidonic acid, eicosatetraenoic acid, eicosapentaenoic acid, docosapentaenoic acid and docosahexaenoic acid; n-6 type unsaturated fatty acids such as linoleic acid, linoelaidic acid, γ-linolenic acid, bis-homo-γ-linolenic acid and arachidonic acid; conjugated fatty acids such as conjugated linoleic acid and α-eleostearic acid; fatty acids carrying double bonds at the 5-position thereof such as pinolenic acid, sciadonic acid, juniperic acid and columbinic acid; polyvalent unsaturated fatty acids, other than those listed above, such as hiragonic acid, moroctic acid, clupanodonic acid and nishinic acid; branched fatty acids such as isobutyric acid, isovaleric acid, iso acid and anti-iso acid; hydroxy fatty acids such as α-hydroxy acid, β-hydroxy acid, mycolic acid and polyhydroxy acid; epoxy-fatty acids; keto-fatty acids; and cyclic fatty acids. In certain embodiments, the lipophilic component also comprises amphiphilic molecules.

The lipid component may constitute about 1-80%, 5-50% (w/v), 10-40% (w/v), or 10-30% (w/v) of the pharmaceutical composition. In certain embodiments, the lipid component constitutes about 10%, about 15%, about 20%, about 25%, about 30% and about 35% (w/v) of the pharmaceutical composition.

Emulsifier

The emulsifier can be any amphiphiles or amphiphilic molecule that will have its hydrophobic tail in the lipophilic core of the micelle and its hydrophilic end in contact with the polar carrier. Examples of emulsifiers are egg phospholipids, pure phospholipids, or amphiphilic peptides.

As used herein, the term "amphiphiles" refers to a chemical compound possessing both hydrophilic and lipophilic properties. Examples of amphiphiles include, but are not limited to, naturally-occurring amphiphiles such as phospholipids, cholesterol, glycolipids, fatty acids, bile acids, and saponins; and synthetic amphiphiles.

Examples of phospholipids include natural or synthetic phospholipids such as phosphatidylcholine, phosphatidylethanolamine, phosphatidylserine, phosphatidic acid, phosphatidylglycerol, phosphatidylinositol, lisophosphatidylcholine, sphingomyelin, egg yolk lecithin, soybean lecithin, and a hydrogenated phospholipid.

Examples of the glycolipids include glyceroglycolipids and sphingoglycolipids. Examples of glyceroglycolipids include digalactosyl diglycerides (such as digalactosyl dilauroyl glyceride, digalactosyl dimyristoyl glyceride, digalactosyl dipalmitoyl glyceride, and digalactosyl distearoyl glyceride) and galactosyl diglycerides (such as galactosyl dilauroyl glyceride, galactosyl dimyristoyl glyceride, galactosyl dipalmitoyl glyceride, and galactosyl distearoyl glyceride). Examples of sphingoglycolipids include galactosyl cerebroside, lactosyl cerebroside, and ganglioside.

Examples of the sterols include cholesterol, cholesterol hemisuccinate, 3β-[N—(N',N'-dimethylaminoethane)carbamoyl]cholesterol, ergosterol, and lanosterol.

In one embodiment, the emulsifier is egg phospholipids. In another embodiment, the emulsifier is soybean lecithin or alpha-phosphatidylcholine.

The emulsifier may constitute about 0.1-5% (w/v) of the pharmaceutical composition. In certain embodiments, the lipid component constitutes about 0.5%, about 0.75%, about 1%, about 1.2%, about 1.5% and about 2% (w/v) of the pharmaceutical composition.

Polar Liquid Carrier

The polar liquid carrier can be any pharmaceutically acceptable polar liquid that is capable of forming an emulsion with the lipid. The term "pharmaceutically acceptable" refers to molecular entities and compositions that are of sufficient purity and quality for use in the formulation of a composition or medicament of the present invention and that, when appropriately administered to an animal or a human, do not produce an adverse, allergic or other untoward reaction. Since both human use (clinical and over-the-counter) and veterinary use are equally included within the scope of the present invention, a pharmaceutically acceptable formulation would include a composition or medicament for either human or veterinary use. In one embodiment, the polar liquid carrier is water or a water based solution. In another embodiment, the polar liquid carrier is a non-aqueous polar liquid such as dimethyl sulfoxide, polyethylene glycol and polar silicone liquids.

A water-based solution generally comprises a physiologically compatible electrolyte vehicle isosmotic or near isosmotic with whole blood. The carrier can be, for example, physiological saline, a saline-glucose mixture, Ringer's solution, lactated Ringer's solution, Locke-Ringer's solution, Krebs-Ringer's solution, Hartmann's balanced saline, heparinized sodium citrate-citric acid-dextrose solution, and polymeric plasma substitutes, such as polyethylene oxide, polyvinyl pyrrolidone, polyvinyl alcohol and ethylene oxide-propylene glycol condensates. The pharmaceutical composition may additionally comprise other constituents such as pharmaceutically-acceptable carriers, diluents, fillers and salts, the selection of which depends on the dosage form utilized, the condition being treated, the particular purpose to be achieved according to the determination of the ordinarily skilled artisan in the field and the properties of such additives.

Gas Carrying Capacity of the Emulsion

The lipid component in the emulsion, in forms such as micelles and/or erythrocyte ghosts provides the ability for the emulsion to carry a larger amount of lipophilic gases than of a purely aqueous solution. Specifically, the lipophilic gases are dissolved into the lipophilic portion of the emulsion to form a homogeneous solution with the lipid component and any other hydrophobic liquid material that may be present in the lipophilic portion of the emulsion.

In one embodiment, the lipophilic gas is oxygen. Oxygen is 4.41 times more soluble in lipid than in water (Battion et al., J. Amer. Oil Chem. Soc. 1968, 45:830-833). Accordingly, an emulsion with a higher lipid content would be able to carry more oxygen than an emulsion with a lesser lipid content. In one embodiment, the emulsion has a lipid content of about 1-80% (w/v). In other embodiments, the emulsion has a lipid content of about 10-80% (w/v), 20-60% (w/v), about 20-50% (w/v), about 20-40% (w/v) or about 20-25% (w/v). In yet another embodiment, the emulsion has a lipid content of about 21.8%. In certain embodiments, the emulsion is prepared by mixing the lipid component and the polar liquid component in the presence of regular air. In other embodiment, the emulsion is further oxygenated by bubbling regular air or pure oxygen through the emulsion for a desired period of time. Since bubbles are undesirable in the circulation due to the possibility of air embolization a bubble trap would have to be added to remove bubbles leaving only the gas that has been solubilized in the core of the micelle, in the polar carrier or attached to proteins or other additives. The gas may also be loaded onto the micelles by equilibration of the micelles with an atmosphere enriched with the gas combined with gentle movement of the emulsion in a mixture chamber in order to avoid the creation of bubbles. Loading may also be done under pressures greater than 1 atmosphere followed by release of the pressure to allow the release of excess gas.

In another embodiment, the lipophilic gas is xenon (Xe) or argon (Ar). In another embodiment, the lipophilic gas is nitric oxide (NO). In another embodiment, the lipophilic gas is hydrogen sulfide ($H_2S$). In yet another embodiment, the lipophilic gas is carbon monoxide (CO).

In one embodiment, the pharmaceutical composition contains micelles loaded with a gas mixture (e.g., a mixture of oxygen, hydrogen sulfide, carbon monoxide and/or nitric oxide). In another embodiment, the [resuscitation] pharmaceutical composition contains a mixture of micelles loaded with various gases. For example, the mixture of micelles may contain 50% NO-loaded micelles and 50% $O_2$-loaded micelles.

Rigid Nonplanar Molecules

The [resuscitation] pharmaceutical composition may further comprise molecules with a rigid nonplanar structure. Such molecules will create greater irregularity and more space for gas molecules in the hydrophobic core of the micelle structure, thereby modifying the gas carrying capacity of the micelles. Examples of such molecules include, but are not limited to, (+) naloxone, (+) morphine, and (+) naltrexone.

In one embodiment, molecules with a rigid nonplanar structure is (+) naloxone which, unlike the opiate receptor antagonist (−) naloxone, does not bind to opiate receptor and will not increase pain as (−) naloxone would. In another embodiment, (+) naloxone is used at a concentration of $10^{-5}$-$10^{-4}$ M. In another embodiment, (+) naloxone is used at a concentration of $10^{-4}$ M or higher.

Upon resuscitation, an inflammatory process may be triggered in reperfused tissues (ischemic—reperfusion injury) causing endothelial cell (EC) injury and capillary leak (CL).

In sepsis and other diseases, systemic inflammation may be triggered by the disease and in a similar sequence leads to EC injury, CL, and ultimately hypovolemic shock that requires resuscitation. Accordingly, in one embodiment, (+) naloxone is used at a concentration range that produces anti-inflammatory effect at $10^{-5}$-$10^{-4}$M (Simpkins C O, Ives N, Tate E, Johnson M. Naloxone inhibits superoxide release from human neutrophils. Life Sci. 1985 Oct. 14; 37(15):1381-6)

Molecules with a nonplanar structure also include organic molecules with branched structures. Examples of such molecules include, but are not limited to, tri-n-octylamine, tri-n-hexylamine, boric acid, tris(3,5,-dimethyl-4-heptyl)ester, metal complexed and non-metal complexed deuteroporphyrin dimethyl esters and their derivatives, hexaphenylsilole, and silicone polymers.

Plasma Component

The pharmaceutical composition may further comprise a plasma component. In one embodiment, the plasma is an animal plasma. In another embodiment, the plasma is human plasma. Although not wishing to be bound by any particular scientific theory, it is believed that the administration of blood substitutes may dilute the concentration of coagulation factors to an undesirable level. Accordingly, using plasma as the diluent for the oxygen carrying component avoids this problem. Plasma can be collected by any means known in the art, provided that red cells, white cells and platelets are essentially removed. Preferably, it is obtained using an automated plasmaphoresis apparatus. Plasmaphoresis apparatuses are commercially available and include, for example, apparatuses that separate plasma from the blood by ultrafiltration or by centrifugation. An ultrafiltration-based plasmaphoresis apparatus such as manufactured by Auto C, A200 (Baxter International Inc., Deerfield, Ill.) is suitable because it effectively removes red cells, white cells and platelets while preserving coagulation factors.

Plasma may be collected with an anticoagulant, many of which are well known in the art. Preferred anti-coagulants are those that chelate calcium such as citrate. In one embodiment, sodium citrate is used as an anticoagulant at a final concentration of 0.2-0.5%, preferably 0.3-0.4%, and most preferably at 0.38%. The plasma may be fresh, frozen, pooled and/or sterilized. While plasma from exogenous sources may be preferred, it is also within the present invention to use autologous plasma that is collected from the subject prior to formulation and administration of the pharmaceutical composition.

In addition to plasma from natural sources, synthetic plasma may also be used. The term "synthetic plasma," as used herein, refers to any aqueous solution that comprises at least one plasma protein. Proteins resembling plasma protein may also be used.

Oncotic Agent

In one embodiment, the pharmaceutical composition further contains an oncotic agent in addition to the lipid micelles. The oncotic agent is comprised of molecules whose size is sufficient to prevent their loss from the circulation by traversing the fenestrations of the capillary bed into the interstitial spaces of the tissues of the body. Examples of oncotic agents include, but are not limited to, dextran (e.g., a low-molecular-weight dextran), dextran derivatives (e.g., carboxymethyl dextran, carboxydextran, cationic dextran, and dextran sulfate), hydroxyethyl starch, hydroxypropyl starch, branched, unsubstituted or substituted starch, gelatin (e.g., modified gelatin), albumin (e.g., human plasma, human serum albumin, heated human plasma protein, and recombinant human serum albumin), PEG, polyvinyl pyrrolidone, carboxymethylcellulose, acacia gum, glucose, a dextrose (e.g., glucose monohydrate), oligosaccharides (e.g., oligosaccharide), a polysaccharide degradation product, an amino acid, and a protein degradation product. Among those, particularly preferable are low-molecular-weight dextran, hydroxyethyl starch, modified gelatin, and recombinant albumin.

Because of its antioxidant effects, albumin may also be used to minimize reactive oxygen species interaction with the components of the micelle and may also stabilize the micelle structure. In one embodiment, the oncotic agent is about 2%, 5%, 7% or 10% (w/v) albumin. In another embodiment, the oncotic agent is a polysaccharide, such as Dextran, in a molecular weight range of 30,000 to 50,000 daltons (D). In yet another embodiment, the oncotic agent is a polysaccharide, such as Dextran, in a molecular weight range of 50,000 to 70,000 D. High molecular weight dextran solutions are more effective in preventing tissue swelling due to their lower rates of leakage from capillaries.

In one embodiment, the concentration of the polysaccharide is sufficient to achieve (when taken together with chloride salts of sodium, calcium and magnesium, organic ion from the organic salt of sodium and hexose sugar discussed above) colloid osmotic pressure approximating that of normal human serum, about 28 mm Hg.

In another embodiment the oncotic agent is glycerol or mannitol in an amount of 2%, 2.5%, 3%, 3.5%, 4%, 4.5% or 5% up to 30% (w/v) of the pharmaceutical composition. In other embodiments, pharmaceutical composition comprises glycerol or mannitol in an amount of 2-5% w/v.

Crystalloid Agent

The pharmaceutical composition may also comprise a crystalloid agent. The crystalloid agent can be any crystalloid which, in the form of the pharmaceutical composition composition, is preferably capable of achieving an osmolarity greater than 800 mOsm/l, i.e. it makes the pharmaceutical composition "hypertonic". Examples of suitable crystalloids and their concentrations in the pharmaceutical composition include, but are not limited to, 3% w/v NaCl, 7% NaCl, 7.5% NaCl, and 7.5% NaCl in 6% w/v dextran. In one embodiment, the [resuscitation] pharmaceutical composition has an osmolarity of between 800 and 2400 mOsm/l.

When the pharmaceutical composition further comprises a crystalloid and is hypertonic, the pharmaceutical composition may provide improved functionality for rapid recovery of hemodynamic parameters over other compositions, which include a colloid component. Small volume highly hypertonic crystalloid infusion (e.g., 1-10 ml/kg) provides significant benefits in the rapid and sustained recovery of acceptable hemodynamic parameters in controlled hemorrhage. In another embodiment, the lipid emulsion used is Intralipid®. In another embodiment, the lipid emulsion used is 20% Intralipid®. In one embodiment, the lipid comprises anti-inflammatory lipids such as omega-3 fatty acids. Hypertonicity may also be achieved by adding glycerol.

Anti-Inflammatory and Immunomodulatory Agent

In one embodiment, the pharmaceutical composition of the present invention further includes an anti-inflammatory or immunomodulatory agent. Examples of the anti-inflammatory agent shown to inhibit reactive oxygen species including, but are not limited to, histidine, albumin, (+) naloxone, prostaglandin $D_2$, molecules of the phenylalkylamine class. Other anti-inflammatory compounds and immunomodulatory drug include interferon; interferon derivatives comprising betaseron, β-interferon; prostane derivatives comprising iloprost, cicaprost; glucocorticoids comprising cortisol, prednisolone, methyl-prednisolone, dexamethasone; immunsuppressives comprising cyclosporine A, methoxsalene, sulfasalazine, azathioprine, methotrexate; lipoxygenase inhibitors comprising zileutone, MK-886, WY-50295, SC-45662, SC-41661A, BI-L-357; leukotriene antagonists; peptide derivatives comprising ACTH and analogs thereof; soluble TNF-receptors; anti-TNF-antibodies; soluble receptors of interleukins or other cytokines; antibodies against receptors of interleukins or other cytokines, T-cell-proteins; and calcipotriols and analogues thereof taken either alone or in combination.

Electrolytes

In one embodiment, the [resuscitation] pharmaceutical composition of the present invention includes one or more electrolytes. The electrolyte to be used in the present invention typically includes various electrolytes to be used for medicinal purposes. Examples of the electrolyte include sodium salts (e.g., sodium chloride, sodium hydrogen carbonate, sodium citrate, sodium lactate, sodium sulfate, sodium dihydrogen phosphate, disodium hydrogen phosphate, sodium acetate, sodium glycerophosphate, sodium carbonate, an amino acid sodium salt, sodium propionate, sodium β-hydroxybutyrate, and sodium gluconate), potassium salts (e.g., potassium chloride, potassium acetate, potassium gluconate, potassium hydrogen carbonate, potassium glycerophosphate, potassium sulfate, potassium lactate, potassium iodide, potassium dihydrogen phosphate, dipotassium hydrogen phosphate, potassium citrate, an amino acid potassium salt, potassium propionate, and potassium β-hydroxybutyrate), calcium salts (e.g., calcium chloride, calcium gluconate, calcium lactate, calcium glycerophosphate, calcium pantothenate, and calcium acetate), magnesium salts (e.g., magnesium chloride, magnesium sulfate, magnesium glycerophosphate, magnesium acetate, magnesium lactate, and an amino acid magnesium salt), ammonium salts (e.g., ammonium chloride), zinc salts (e.g., zinc sulfate, zinc chloride, zinc gluconate, zinc lactate, and zinc acetate), iron salts (e.g., iron sulfate, iron chloride, and iron gluconate), copper salts (e.g., copper sulfate), and manganese salts (for example, manganese sulfate). Among those, particularly preferable are sodium chloride, potassium chloride, magnesium chloride, disodium hydrogen phosphate, dipotassium hydrogen phosphate, potassium dihydrogen phosphate, sodium lactate, sodium acetate, sodium citrate, potassium acetate, potassium glycerophosphate, calcium gluconate, calcium chloride, magnesium sulfate, and zinc sulfate.

Concentration of calcium, sodium, magnesium and potassium ion is typically within the range of normal physiological concentrations of said ions in plasma. In general, the desired concentration of these ions is obtained from the dissolved chloride salts of calcium, sodium and magnesium. The sodium ions may also come from a dissolved organic salt of sodium that is also in solution.

In one embodiment, the sodium ion concentration is in a range from 70 mM to about 160 mM. In another embodiment, the sodium ion concentration is in a range of about 130 to 150 mM.

In one embodiment, the concentration of calcium ion is in a range of about 0.5 mM to 4.0 mM. In another embodiment, the concentration of calcium ion is in a range of about 2.0 mM to 2.5 mM.

In one embodiment, the concentration of magnesium ion is in a range of 0 to 10 mM. In another embodiment, the concentration of magnesium ion is in a range of about 0.3 mM to 0.45 mM. It is best not to include excessive amounts of magnesium ion in the [resuscitation] pharmaceutical composition of the invention because high magnesium ion concentrations negatively affect the strength of cardiac contractile activity. In a preferred embodiment of the invention, the solution contains subphysiological amounts of magnesium ion.

In one embodiment, the concentration of potassium ion is in a subphysiological range of between 0-5 mEq/l $K^+$ (0-5 mM), preferably 2-3 mEq/l $K^+$ (2-3 mM). Thus, the pharmaceutical composition allows for dilution of the potassium ion concentration in stored transfused blood. As a result, high concentrations of potassium ion and potential cardiac arrhythmias and cardiac insufficiency caused thereby can be more easily controlled. The pharmaceutical composition containing a subphysiological amount of potassium is also useful for purposes of blood substitution and low temperature maintenance of a subject.

In one embodiment, the concentration of chloride ion is in the range of 70 mM to 160 mM. In another embodiment, the concentration of chloride ion is in the range of 110 mM to 125 mM.

Other sources of ions include sodium salts (e.g., sodium hydrogen carbonate, sodium citrate, sodium lactate, sodium sulfate, sodium dihydrogen phosphate, disodium hydrogen phosphate, sodium acetate, sodium glycerophosphate, sodium carbonate, an amino acid sodium salt, sodium propionate, sodium β-hydroxybutyrate, and sodium gluconate), potassium salts (e.g., potassium acetate, potassium gluconate, potassium hydrogen carbonate, potassium glycerophosphate, potassium sulfate, potassium lactate, potassium iodide, potassium dihydrogen phosphate, dipotassium hydrogen phosphate, potassium citrate, an amino acid potassium salt, potassium propionate, and potassium β-hydroxybutyrate), calcium salts (e.g., calcium gluconate, calcium lactate, calcium glycerophosphate, calcium pantothenate, and calcium acetate), magnesium salts (e.g., magnesium sulfate, magnesium glycerophosphate, magnesium acetate, magnesium lactate, and an amino acid magnesium salt), ammonium salts, zinc salts (e.g., zinc sulfate, zinc chloride, zinc gluconate, zinc lactate, and zinc acetate), iron salts (e.g., iron sulfate, iron chloride, and iron gluconate), copper salts (e.g., copper sulfate), and manganese salts (for example, manganese sulfate). Among those, particularly preferable are sodium chloride, potassium chloride, magnesium chloride, disodium hydrogen phosphate, dipotassium hydrogen phosphate, potassium dihydrogen phosphate, sodium lactate, sodium acetate, sodium citrate, potassium acetate, potassium glycerophosphate, calcium gluconate, calcium chloride, magnesium sulfate, choline chloride and zinc sulfate.

Carbohydrates and Amino Acids

The pharmaceutical composition may contain a carbohydrate or a mixture of carbohydrates. Suitable carbohydrates include, but are not limited to, simple hexose (e.g., glucose, fructose and galactose), mannitol, sorbitol or others known to the art. In one embodiment, the pharmaceutical composition includes physiological levels of a hexose. "Physiological levels of a hexose" includes a hexose concentration of between 2 mM to 50 mM. In one embodiment, the pharmaceutical composition contains 5 mM glucose. At times, it is desirable to increase the concentration of hexose in order to provide nutrition to cells. Thus the range of hexose may be expanded up to about 50 mM if necessary to provide minimal calories for nutrition.

Other suitable carbohydrates include various saccharides to be used for medicinal purposes. Examples of the saccharides include xylitol, dextrin, glycerin, sucrose, trehalose, glycerol, maltose, lactose, and erythritol.

The pharmaceutical composition may contain an amino acid or a mixture of amino acids. Suitable amino acids include, but are not limited to, alanine, arginine, aspartate, asparagine, cysteine, glutamate, glutamine, glycine, histidine, isoleuc leucine, lysine, methionine, phenylalanine, proline, serine, threonine, tryptophan, tyrosine, threonine, tryptophan, valine and 2-aminopentaenoic acid. In one embodiment, the amino acid is selected from the group consisting of histidine, tyrosine, phenylalanine and cysteine. In another embodiment, the pharmaceutical composition comprises an amino acids known to prevent apoptosis. Examples of such amino acids include glutamine, glycine, proline and 2-aminopentaenoic acid.

The amino acid may be used in the concentration range of 0.1 fM-200 mM, 0.1 fM-100 pM, 100 pM-10 nM, 10 nM-10 μM, 0.01-200 mM, 0.2-50 mM, or 0.5-2 mM. In one embodiment, the amino acid is used at a concentration of 1 mM.

Buffering Agent

The pharmaceutical composition of the present invention may further comprise a biological buffer to maintain the pH of the fluid at the physiological range of pH7-8. Examples of biological buffers include, but are not limited to, N-2-Hydroxyethylpiperazine-N'-2-hydroxypropanesulfonic acid (HEPES), 3-(N-Morpholino)propanesulfonic acid (MOPS), 2-([2-Hydroxy-1,1-bis(hydroxymethyl)ethyl]amino)glyci ethanesulfonic acid (TES), 3-[N-tris(Hydroxy-methyl)methylamino]-2-hydroxyethyl]-1-piperazinep ropanesulfonic acid (EPPS), Tris[hydrolymethyl]-aminoethane (THAM), and Tris[Hydroxylmethyl]methyl aminomethane (TRIS).

In one embodiment, the buffering agent is histidine, imidazole, substituted histidine or imidazole compounds retaining the amphoteric site of the imidazole ring, oligopeptides containing histidine, or glycyglycine or mixtures thereof. Histidine is also capable of reducing reactive oxygen species and inhibiting cell shrinkage. (see e.g., Simpkins et al., J. Trauma. 2007, 63:565-572). Histidine or imidazole may be used in a concentration range of about 0.0001M to about 0.2M, preferably about 0.0001M to about 0.01M. In one embodiment, histidine is used at a concentration of about 1 mM.

In another embodiment, the pharmaceutical composition of the present invention uses normal biological components to maintain in vivo biological pH. Briefly, some biological compounds, such as lactate, are capable of being metabolized in vivo and act with other biological components to maintain a biologically appropriate pH in an animal. The biological components are effective in maintaining a biologically appropriate pH even at hypothermic temperatures and at essentially bloodless conditions. Examples of the normal biological components include, but are not limited to carboxylic acids, salt and ester thereof. Carboxylic acids have the general structural formula of RCOOX, where R is an alkyl, alkenyl, or aryl, branched or straight chained, containing 1 to 30 carbons which carbons may be substituted, and X is hydrogen or sodium or other biologically compatible ion substituent which can attach at the oxygen position, or is a short straight or branched chain alkyl containing 1-4 carbons, e.g., —CH$_3$, —CH$_2$CH$_3$. Examples of carboxylic acids and carboxylic acid salts include, but are not limited to, lactate and sodium lactate, citrate and sodium citrate, gluconate and sodium gluconate, pyruvate and sodium pyruvate, succinate and sodium succinate, and acetate and sodium acetate.

Coagulation Enhancers

Aggressive high volume resuscitation, without controlling the bleeding, can exacerbate the hemorrhage by disrupting the early formed soft thrombi, and by diluting coagulation factors. In certain embodiments, the pharmaceutical composition may further comprise one or more coagulation enhancers. Examples of coagulation factors include, but are not limited to, factor 7, thrombin and platelets. These factors may be from natural or non-natural sources. In certain embodiments, factor 7 is added to the pharmaceutical composition at a concentration of 70-150 IU/kg, prothrombin complex is added to the pharmaceutical composition at a concentration of 15-40 IU/kg, and fibrinogen is added to the [resuscitation] pharmaceutical composition at a concentration of 50-90 mg/kg. Naturally-derived or synthetic platelets or platelet substitutes may also be added.

Antioxidants

In certain embodiments, the pharmaceutical composition may further comprise one or more antioxidants. Examples of antioxidants include, but are not limited to, sodium hydrogen sulfite, sodium sulfite, sodium pyrosulfite (e.g., sodium metabisulfite), rongalite (CH2OHSO2Na), ascorbic acid, sodium ascorbate, erythorbic acid, sodium erythorbate, cysteine, cysteine hydrochloride, homocysteine, glutathione, thioglycerol, α-thioglycerin, sodium edetate, citric acid, isopropyl citrate, potassium dichloroisocyanurate, sodium thioglycolate, sodium pyrosulfite 1,3-butylene glycol, disodium calcium ethylenediaminetetraacetate, disodium ethylenediaminetetraacetate, an amino acid sulfite (e.g, L-lysine sulfite), butylhydroxyanisole (BHA), butylhydroxytoluene (BHT), propyl gallate, ascorbyl palmitate, vitamin E and derivatives thereof (e.g., dl-α-tocopherol, tocopherol acetate, natural vitamin E, d-δ-tocopherol, mixed tocopherol, and trolox), guaiac, nordihydroguaiaretic acid (NDGA), L-ascorbate stearate esters, soybean lecithin, palmitic acid ascorbic acid, benzotriazol, and pentaerythrityl-tetrakis[3-(3,5-di-t-butyl-4-hydroxyphenyepropionate]2-mercaptobenzimidazole. Among those, preferable are sodium hydrogen sulfite, sodium sulfite, ascorbic acid, homocysteine, dl-α-tocopherol, tocopherol acetate, glutathione, and trolox.

Other Components

In addition to the components discussed above, the pharmaceutical composition may further comprise other additives that include, but are not limited to, antibiotics, such as penicillin, cloxacillin, dicloxacillin, cephalosporin, erythromycin, amoxicillin-clavulanate, ampicillin, tetracycline, trimethoprim-sulfamethoxazole, chloramphenicol, ciprofloxacin, aminoglycoside (e.g., tobramycin and gentamicin), streptomycin, sulfa drugs, kanamycin, neomycin, land monobactams; anti-viral agents, such as amantadine hydrochloride, rimantadin, acyclovir, famciclovir, foscarnet, ganciclovir sodium, idoxuridine, ribavirin, sorivudine, trifluridine, valacyclovir, valgancyclovir, pencyclovir, vidarabin, didanosine, stavudine, zalcitabine, zidovudine, interferon alpha, and edoxudine; anti-fungal agents such as terbinafine hydrochloride, nystatin, amphotericin B, griseofulvin, ketoconazole, miconazole nitrate, flucytosine, fluconazole, itraconazole, clotrimazole, benzoic acid, salicylic acid, voriconazole, caspofungin, and selenium sulfide; vitamins, amino acids, vessel expanders such as alcohols and polyalcohols, surfactants, antibodies against harmful cytokines such as tumor necrosis factor (TNF) or interleukins, and mediators of vascular potency and immunomoduators, such as prostaglandins, leukotrienes, pro-opiomelanocortin fragments and platelet activating factors.

In certain embodiments, the pharmaceutical composition may further contain beneficial anions such as lactate or glutamate. Hypertonic lactate containing compositions have been found to be effective in reducing brain edema in patients with acute hemodynamic distress. In one embodiment, the pharmaceutical composition contains 250 to 2400 mM of lactic acid or lactate. In another embodiment, the pharmaceutical composition contains 250 to 2400 mM of lactic acid or lactate and 2 to 10 mM potassium.

In certain other embodiments, the pharmaceutical composition may contain substituted cations. For example, the pharmaceutical composition may contain choline to substitute sodium ions.

In certain embodiments, the pharmaceutical composition further contains anti-cancer drugs and/or intracellular signal molecules, such as cAMP and diacylglycerol. In other embodiments, the pharmaceutical composition further contain one or more organelles or organelle components such as endoplasmic reticulum, ribosomes, and mitochondria in whole or in part.

In other embodiments, the pharmaceutical composition may be combined with red blood cells, modified red blood cells or other cellular components of blood.

In yet other embodiments, the pharmaceutical composition further comprises proopiomelanocortin fragments, such as beta endorphin, melonocyte stimulating hormone enkephalins or opiates to modify the immune response and to provide analgesia. Beta endorphin may also be used at a final concentration of 0.01-100 nm, preferably 0.1-10 nm, more preferably about 1 nm, to modulate neutrophilic function in the septic state (See, e.g., Simpkins et al., J Natl Med. Assoc. 1988, 80: 199-203).

In yet other embodiments, the pharmaceutical composition further comprises one or more neurotropic agents for treatment of psychiatric disease or prevention of psychiatric disease.

The pharmaceutical composition possesses the ability to absorb toxic chemical molecules/biomolecules produced as the result of trauma or hemorrhagic shock. For example, lymph factors produced in gut and thoracic duct lymph nodes may result in acute lung injury and red blood cell deformability after trauma/hemorrhagic shock. Other toxic chemical molecules/biomolecules include, but are not limited to, leukotrienes, prostaglandins, nitric oxide, endotoxin and tumor necrosis factor (TNF). The lipid emulsion in the pharmaceutical composition allows effective absorption of lipophilic chemical molecules/biomolecules. In certain embodiment, the pharmaceutical composition further contains antagonists to toxic chemical molecules/biomolecules, such as antibodies to endotoxins.

In one embodiment, the pharmaceutical composition comprises 10-50% (w/v) soybean oil, 1-1.5% (w/v) soybean lecithin and 1-1.5% (w/v) glycerol. In another embodiment, the pharmaceutical composition further comprises 10-30% (w/v) soybean oil, 1-1.5% (w/v) soybean lecithin, 1-1.5% (w/v) glycerol, 102 mM NaCl, 28 mM Na(L) lactate, and 4 mM KCL. In another embodiment, the pharmaceutical composition further comprises 10-30% (w/v) soybean oil, 1-1.5% (w/v) soybean lecithin, 1-1.5% (w/v) glycerol, 102 mM NaCl, 28 mM Na(L) lactate, 4 mM KCL and 1 mM histidine, tyrosine, phenylalanine or cysteine. The pharmaceutical composition is prepared under conditions that form micelles with an average diameter of 5 µm or smaller. In one embodiment, the micelles in the pharmaceutical composition have an average diameter of 1 µm or smaller. In another embodiment, the micelles in the pharmaceutical composition have an average diameter of 0.3 µm or smaller. In another embodiment, the micelles in the pharmaceutical composition have an average diameter of 0.1 µm or smaller. In another embodiment, the micelles in the pharmaceutical composition have an average diameter of 0.03 µm or smaller. In yet another embodiment, the micelles in the pharmaceutical composition have an average diameter of 0.01 µm or smaller. In another embodiment the hydrophobic component is carried within erythrocyte ghosts. Other oils such as oil from chia beans, pumpkin seeds or other sources may be used to take advantage of their ability to modulate negatively or positively the processes of coagulation, proliferation, immune response or nutrition as needed by the disease process being addressed. In certain embodiments, the above described pharmaceutical composition further comprise about 2-40% (w/v), about 2-20% (w/v), about 4-10% (w/v), or about 5% (w/v) albumin or albumin polymers or albumin polymers conjugated with amino acids or peptides, which are added to the pharmaceutical composition after the formation of micelles.

In certain embodiments the pharmaceutical composition of the present invention comprises a lipid component selected from the group consisting of soybean oil, chia bean oil and algae oil, an emulsifier selected from the group consisting of phospholipids and α-phosphatidylcholine, and an amino acid or n-acetyl amino acid at a final concentration of 0.2-20 mM, 0.5-10 mM, 0.5-5 mM or 0.5-2 mM. In certain embodiments, the pharmaceutical composition has an final amino acid concentration of 0.1, 0.2, 0.5, 1, 2.5, 5, 7.5, or 10 mM. The emulsifier:the lipid component ratio (w/w) is about 1:400 to about 1:20, preferably about 1:200 to about 1:50. In one embodiment, the emulsifier:the lipid component ratio (w/w) is about 1:100. In another embodiment, the emulsifier:the lipid component ratio (w/w) is about 1.2:100.

The pharmaceutical composition is free of $Ca^{++}$, $K^+$, and $Mg^{++}$ and $Al^{+++}$, as well as hemoglobin, derivatives of hemoglobin, perfluorocarbon and derivatives of perfluorocarbon. In certain embodiments, $Ca^{++}$ and $K^+$ are added to the pharmaceutical composition just prior to use (e.g., within 24 hours prior to use). Because $Al^{+++}$ is toxic to bone, brain, hematopoiesis, heme synthesis, globulin synthesis, iron absorption and metabolism, and fetal development, all oils and other components must have the minimum amount of $Al^{+++}$ possible. In certain embodiments, the pharmaceutical composition contains $Al^{+++}$ at a concentration of less than 25 mg/l, 20 mg/l, 10 mg/l or 5 mg/l. In other embodiments, the pharmaceutical composition is free of $Al^{+++}$, i.e., undetectable by conventional methods.

In one embodiment, the pharmaceutical composition comprises soybean oil, egg yolk phospholipids and an amino acid, beta-endorphin or other modulator that acts at femtomolar concentrations or higher at a final concentration of 0.1 femtomolar (fM) to 10 mM.

Preparation of the Pharmaceutical Composition

The pharmaceutical composition may be prepared by mixing the lipid component, the emulsifier, the aqueous carrier, and any other components to form an emulsion. Commonly used mixing methods include, but are not limited to, stirring, shaking, homogenization, vibration, microfluidization and sonication. In one embodiment, the pharmaceutical composition is formed by mixing a pre-formed lipid emulsion, such as Intralipid® or Liposyn® with the aqueous carrier and other components. In addition, the pharmaceutical composition can be carried in erythrocyte ghosts. Specifically, the emulsion should be prepared in manners that allow the lipophilic gases dissolving into the lipophilic portion of the emulsion but not forming microbubbles which may increase the risk of gas embolization.

In certain embodiments, albumin or albumin polymers or albumin polymers conjugated with amino acids or peptides is added to the pharmaceutical composition in an amount of 2-40% (w/v), about 2-20% (w/v), about 4-10% (w/v), or about 5% (w/v). The albumin or albumin polymers or albumin polymers conjugated with amino acids or peptides is added to the pharmaceutical composition after the formation of micelles. In one embodiment, the lipid component, the emulsifier, the aqueous carrier and any other non-albumin components are mixed to form an emulsion. Albumin, albumin polymers or albumin polymers conjugated with amino acids or peptides is then dissolved in the emulsion at the desired concentration.

In one embodiment, the pharmaceutical composition is prepared according to the following recipes:

Recipe 1
Part A
soybean oil 20%=20 grams
glycerol 2.25%=2.25 grams
egg yolk phospholipids 2.4%=2.4 grams
add water to final volume of 100 ml
add sodium hydroxide until pH=8.0
stir or sonicate to produce micelles with average diameter of 300-400 nm
Part B
NaCl 102 mM=0.6 grams
Na (L) lactate 28 mM=0.31 grams
KCl 4 mM=0.03 grams
$CaCl_2$ 1.5 mM=0.06 grams
Human serum albumin 5%=5 grams
Part A may be used alone, or mixed with Part B within 24 hours of use.

Recipe 2
Part A
Soybean oil 20%=20 grams
Glycerol 2.25%=2.25 grams
Egg yolk phospholipids 2.4%=2.4 grams add water to final volume of 100 ml
add sodium hydroxide until pH=8.0
stir or sonicate to produce micelles with average diameter of 300-400 nm
Part B
NaCl 102 mM=0.6 grams
Na (L) lactate 28 mM=0.31 grams
KCl 4 mM=0.03 grams
CaCl2 1.5 mM=0.06 grams
1 mM amino acid histidine or cysteine
β-endorphin 1 nM
Part A may be used alone, or mixed with Part B within 24 hours of use.

In some embodiments, Part A or the mixture of Part A and Part B, is loaded with oxygen, nitric oxide, carbon monoxide, xenon, argon, hydrogen sulfide other hydrophobic gases or mixtures of these gases prior to use. These gases may be used in shock to deliver oxygen for aerobic metabolism after the initial bolus, provide an initial carbon monoxide bolus to protect against reperfusion injury, to open vessels in vascular diseases or states involving vascular constriction or obstruction, xenon or argon to protect against the effects of traumatic brain injury or seizures, or hydrogen sulfide to promote long-term tissue preservation. Nitric oxide loaded micelles may also be used as an anti-hypertensive medication. Either Part A, Part B, or the mixture of Part A and Part B can be sterilized by autoclaving.

In some embodiments, the soybean oil, which enhances clotting, is replaced with chia bean oil which is anti-inflammatory and reduces clotting. In one embodiment, a pharmaceutical composition with soybean oil is used in initial phase of the infusion in which bleeding is occurring. A pharmaceutical composition with chia bean oil is used for later stages of the infusion when bleeding is no longer an issue an issue.

In some other embodiments, the glycerol in Part A is replaced with mannitol. In other embodiments, the egg phospholipids is replaced with α-phosphatidylcholine to eliminate source of protein contamination and anaphylaxis due to contamination of egg phospholipid with egg protein. In yet other embodiments, the amino acids in Part B of Recipe 2 is replaced with N-acetyl amino acids.

In one embodiment, the pharmaceutical composition is a non-oxygenated pharmaceutical composition. As used herein, the term "non-oxygenated pharmaceutical composition" refers to a formulation that is prepared in atmospheric air and is not loaded with oxygen by any oxygenation device or method.

In certain embodiments, the pharmaceutical composition may be loaded with a lipophilic gas prior to clinical application. Examples of such gases include, but are not limited to, oxygen, xenon, argon, nitric oxide, carbon monoxide, hydrogen sulfide. As used herein, "a pharmaceutical composition loaded with a lipophilic gas" refers to a pharmaceutical composition that has been subjected to a process to increase the content of such lipophilic gas in the pharmaceutical composition. A pharmaceutical composition may be loaded with a lipophilic gas by bubbling the lipophilic gas through the pharmaceutical composition for a desired period of time, or by agitating the pharmaceutical composition in the presence of the lipophilic gas under pressure.

In one embodiment, the pharmaceutical composition is oxygenated by bubbling pure oxygen or a gas with an oxygen content in the range of 21% to 100% (v/v), preferably 40% to 100% (v/v), more preferably 60% to 100% (v/v), and most preferably 80% to 100% (v/v), through the mixture for a period of 30 seconds or longer, preferably 1-15 minutes, more preferably 1-5 minutes. Oxygen may also be added under pressure followed by a reduction of the pressure to one atmosphere. In one embodiment, the pharmaceutical composition is oxygenated immediately prior to application. The pharmaceutical composition may be oxygenated using portable oxygen tanks or portable oxygen concentrators, such the Evergo Portable Pulse Dose Oxygen concentrator produced by Philips Healthcare at Andover, Mass.

Another method could be allowing the emulsion to equilibrate with an atmosphere filled with the gas that is to be added. In most cases a bubble trap would be necessary to remove bubbles that could become gas emboli. The equilibration time for a pharmaceutical composition of a particular composition may be determined experimentally.

In one embodiment, the pharmaceutical composition comprises an oxygenated lipid emulsion. As used herein, the term "oxygenated lipid emulsion' or "oxygenated pharmaceutical composition" refers to a specific type of gassed lipid emulsion or gassed fluid which has been forced to absorb oxygen such that the total concentration of oxygen contained therein is greater than that present in the same liquid at atmospheric equilibrium conditions.

Kits

Another aspect of the present invention relates to a resuscitation kit. In one embodiment, the resuscitation kit comprises an oxygenated pharmaceutical composition and at least one additive. Examples of additives include, but are not limited to, oncotic agent, crystalloid agent, vessel expander, cardioplegic, or cardiotonic agent scavengers of free radicals or mediators, cell signaling modulators, and receptor agonists or antagonists. In another experiment, the kit further contains an intravenous infusion (IV) set. In another embodiment, the oxygenated pharmaceutical composition is contained in one or more preloaded syringes for emergency application.

In another embodiment, the kit contains a pharmaceutical composition and a portable oxygen container that can be used to re-oxygenate the pharmaceutical composition immediately prior to application. The oxygen container may contain pure oxygen, or a gas mixture of oxygen with hydrogen sulfide and/or carbon monoxide and/or nitric oxide. In another embodiment, the kit contains a pharmaceutical composition, and an air pump for oxygenating the pharmaceutical composition with ambient air immediately prior to application.

In another embodiment, the kit contains pharmaceutical composition and a portable oxygen concentrator for oxygenating the pharmaceutical composition with oxygen filtered from ambient air immediately prior to application. In one embodiment, the portable oxygen concentrator is an Evergo Portable Pulse Dose Oxygen concentrator produced by Philips Healthcare at Andover, Mass.

In another embodiment, the kit contains a pharmaceutical composition and an oxygen producing canister that is capable of producing oxygen through a chemical reaction. Chemicals that may be used for the production of oxygen include, but are not limited to, sodium chlorate, sodium peroxide and potassium superoxide.

In another embodiment, the kit further contains a bubble removing device, such as a bubble trap.

In another embodiment, the kit contains syringes that are prefilled with the pharmaceutical composition of the present invention and are ready to be pushed into the blood stream of shock patients. In certain embodiment, the syringes have volumes of 60-500 cc. In other embodiments, the syringes also come with delivery tubing. The pharmaceutical composition may also be preloaded with oxygen, some other gas or other beneficial substances. In another embodiment, the kit contains cartridges that are prefilled with the pharmaceutical composition of the present invention. The cartridges can be snapped into an apparatus that would infuse the pharmaceutical composition into a patient at a desired rate.

Treatment Methods

Another aspect of the present invention relates to a method for treating conditions related to lack of blood supply with a lipid-based pharmaceutical composition. Conditions related to a lack of blood supply include, but are not limited to, hypovolemia, ischemia, hemodilution, trauma, septic shock, cancer, anemia, cardioplegia, hypoxia and organ perfusion. The term "hypovolemia," as used herein, refers to an abnormally decreased volume of circulating fluid (blood or plasma) in the body. This condition may result from "hemorrhage," or the escape of blood from the vessels. The term "ischemia," as used herein, refers to a deficiency of blood in a part of the body, usually caused by a functional constriction or actual obstruction of a blood vessel. Conditions related to lack of blood supply also include situations in which the intravascular volume may be normal but blood vessels are dilated. Examples are septic shock in which mediators such as endothelium-derived relaxing factors cause blood vessel tone and responsiveness to catecholamines to decrease. Examples of an endothelium-derived relaxing factor is nitric oxide. Prostaglandin E is another molecule that dilates blood vessels.

The pharmaceutical composition may be administered intravenously, intra-arterially or intra cardiac to a subject in need of such treatment. Administration of the pharmaceutical composition can occur for a period of seconds, hours, days or weeks depending on the purpose of the pharmaceutical composition usage, the ability to control blood loss or the ability to restore spontaneous cardiac contraction. For example, when used as a blood volume expander and an oxygen carrier for the treatment of severe hemorrhage shock, the usual time course of administration is as rapidly as possible, which may range from about 1 ml/kg/hour to about 150 ml/kg/min or from about 10 ml/kg/min to about 150 ml/kg/min. For the treatment of severe hemorrhagic shock, the pharmaceutical composition is given in an amount and at an infusion rate that is sufficient to raise the blood pressure in the patient. In certain embodiments, the pharmaceutical composition is given in an amount of 500-4000 ml, 500-2000 ml, 500-1000 ml, 1000-4000 ml and 1000-2000 ml. In certain embodiments, the pharmaceutical composition is given in an amount that equals to about 10%, 15%, 20%, 25%, 30%, 35%, 40%, 45%, 50%, 55% 60%, 65%, 70%, 75%, 80%, 85% or 90% of the normal blood volume of a patient in a period of 30-300 seconds. In certain embodiments, the pharmaceutical composition is given at a rate of 200-4000 ml/min. In other embodiments, the pharmaceutical composition is given at a rate of about 1000-4000 ml/min. In other embodiments, the pharmaceutical composition is given at a rate of about 200-2000 ml/min. In other embodiments, the pharmaceutical composition is given at a rate of about 100-1000 ml/min. In yet other embodiments, the pharmaceutical composition is given at a rate of about 500-700 ml/min. In some embodiments, the pharmaceutical composition is given without oxygenation. In other embodiments, the pharmaceutical composition is an oxygenated pharmaceutical composition. The infusion rate may vary from a low of 5 ml/min to 120 liters/hour. There is no upper limit of volume or rate due to the fact that blood loss can be massive and the infusion of the pharmaceutical composition would be given at a rate and volume necessary to provide sufficient perfusion of tissues and tissue viability.

Another aspect of the present invention relates to a method for increasing blood pressure in a subject in need of such treatment. In certain embodiment, the blood pressure refers to systolic pressure. The method comprises administering into the patient an effective amount of the pharmaceutical composition of the present invention. In one embodiment, the subject is a mammal who lost at least 15% of its blood volume. In another embodiment, the subject is a mammal who lost 15% to 30% of its blood volume. In another embodiment, the subject is a mammal who lost at least 30% of its blood volume. In another embodiment, the subject is a mammal who lost 30% to 40% of its blood volume. In another embodiment, the subject is a mammal who lost at least 40% of its blood volume. In another embodiment, the subject is in hemorrhagic shock. In yet another embodiment, the subject is in severe hemorrhagic shock. As used herein, the term "hemorrhagic shock" refers to a shock status induced by the loss of at least 15% of the blood volume. As used herein, the term "severe hemorrhagic shock" refers to a shock status induced by the loss of at least 30% of the blood volume.

In one embodiment, the "effective amount" of the pharmaceutical composition needed to increase the blood pressure in a subject with hemorrhagic shock or severe hemorrhagic shock is 40%, 50%, 60%, 70%, 80%, 90%, 100%, 120%, 150%, 200% or 300% of the lost blood volume. Typically, the pharmaceutical composition is infused initially at a volume that equals to at least 40%, 50%, 60%, 70% 80%, 90% or 100% of the lost blood volume to raise the blood pressure. A larger amount (e.g., 150% to 300% or even more) is given on an as needed basis.

In another embodiment, the "effective amount" of the pharmaceutical composition needed to increase the blood pressure in a subject with hemorrhagic shock or severe hemorrhagic shock is the amount needed to restore the systolic pressure of the subject to 70 mmHg, 80 mmHg, 90 mmHg, or higher.

Other hemodynamic parameters, such as perfusion of brain, kidneys, heart, muscle, spleen or other tissues, cardiac output, stroke volume index, mitochondrial oxidative phosphorylation followed by near infrared spectroscopy or other means, blood lactate or membrane polarization, may also be used to determine the "effective amount" of the pharmaceutical composition needed to increase the blood pressure in a subject.

While the pharmaceutical composition of the present invention is being administered to and circulated through the subject, various agents such as cardioplegic or cardiotonic agents may be administered either directly into the subject's circulatory system, administered directly to the subject's myocardium, or added to the pharmaceutical composition the present invention. These components are added to achieve desired physiological effects such as maintaining regular cardiac contractile activity, stopping cardiac fibrillation or completely inhibiting contractile activity of the myocardium or heart muscle.

Cardioplegic agents are materials that cause myocardial contraction to cease and include anesthetics such as lidocaine, procaine and novocaine and monovalent cations such as potassium ion in concentrations sufficient to achieve myocardial contractile inhibition. Concentrations of potassium ion sufficient to achieve this effect are generally in excess of 15 mM.

During revival of a subject, the subject may be re-infused with a mixture of the pharmaceutical composition described along with blood retained from the subject or obtained from blood donors. Whole blood is infused until the subject achieves an acceptable hematocrit, generally equal to or exceeding hematocrits of about 30% and the goals of resuscitation such as a normal lactate or mixed venous oxygen saturation of between 60% and 76% have been achieved. When these goals have been achieved, rapid infusion is discontinued and the subject is revived after closure of surgical wounds using conventional procedures. In certain embodiments, the pharmaceutical composition of the present invention is used to treat shock, including but are not limited to, neurogenic shock, cardiogenic shock, adrenal insufficiency shock and septic shock.

Another aspect of this invention is ability to increase blood pressure by reversible absorption of nitric oxide. Hemoglobin and nitric oxide synthase inhibitors are very effective at removing nitric oxide. However they do not readily lead to the release of nitric oxide. Such potent and irreversible uptake of nitric oxide can lead to lethal vasoconstriction even as the blood pressure increases. In contrast, the pharmaceutical composition takes up nitric oxide because of the greater solubility of nitric oxide in lipids. This mechanism is not as potent as the aforementioned methods and it is highly reversible. This mechanism method provides a variable reservoir of nitric oxide that may take up or release nitric oxide in a way that varies with local concentrations of nitric oxide.

In certain other embodiments, the pharmaceutical composition is administered. intraperitonealy, transdermally, enterally, rectally and by inhalation.

Another aspect of the present invention relates to a method of using the pharmaceutical composition described above to oxygenate patients whose lungs are severely damaged and unable to absorb oxygen even with special modes of ventilation. The oxygen loaded pharmaceutical composition may deliver oxygen to tissues via circulation and allows the lung to recover from the damage. In this regard, the pharmaceutical composition may be used to replace extracorporeal membrane oxygenation (ECMO).

Another aspect of the present invention relates to a method of using the pharmaceutical composition in exchange transfusion and whole circulation perfusion to wash out blood containing harmful materials such as infectious agents, cancerous agents, and toxic agents. In both cases, the pharmaceutical composition may comprise an emulsion consisting of 20% lipid micelles and isotonic saline with or without albumin. The pharmaceutical composition may also be used to absorb toxic chemical molecules/biomolecules produced as the result of trauma, hemorrhagic shock or other form of shocks. Oxygen or other gases may or may not be added.

Treatment of Seizure or Neuronal Injuries with Xenon/Argon-Carrying Pharmaceutical Composition Another aspect of the present invention relates to a method for treating seizure or neuronal injury using xenon or argon carried by the pharmaceutical composition of the present invention. Xenon is colorless, heavy, odorless noble gas. Xenon has been used as a general anaesthetic. Two physiological mechanisms for xenon anesthesia have been proposed. The first one involves the inhibition of the calcium ATPase pump—the mechanism cells use to remove calcium ($Ca^{2+}$)—in the cell membrane of synapses (see e.g., Franks, J J et al. *Anesthesiology* 82:108-117). The second mechanism involves the non-specific interactions between the anesthetic and the lipid membrane (see, e.g., Heimburg, T and Jackson A D, 2007, *Biophysical Journal* 92:3159-65. Xenon has a minimum alveolar concentration (MAC) of 71%, making it 50% more potent than $N_2O$ as an anesthetic. Thus it can be used in concentrations with oxygen that have a lower risk of hypoxia.

Xenon is also an antagonist of N-methyl-d-aspartate receptors (NMDA receptors) and can be used to treat brain injuries. The NMDA receptors exacerbate the damage from oxygen deprivation and xenon performs better as a neuroprotectant than either ketamine or nitrous oxide, which have undesired side-effects (Ma, D.; et al., 2002, *British Journal of Anaesthesia* 89:739-746).

Without being bound by any theory, it is believed that glutamate excitotoxicity is involved in the development of injury in conditions such as traumatic brain injury and ischemia/stroke and that xenon neuroprotection is mediated by competitive inhibition of the NMDA receptor at its glycine-binding site.

Argon (Ar) is another noble gas that has shown neuroprotective properties in in vitro models of cerebral ischemia and traumatic brain injury (Loetscher et al., Crit. Care 2009, 13:R206).

In one embodiment, a xenon- or argon-carrying pharmaceutical composition is used to treat seizure, neuronal injuries and/or brain ischemia in a subject. The treatment comprises: infusing a sufficient amount of a xenon- or argon-carrying pharmaceutical composition into said subject for a desired period of time. The xenon- or argon-carrying pharmaceutical composition may be produced by mixing degased lipid component and degased polar liquid in a container filled with xenon, or by bubbling xenon through a degassed pharmaceutical composition. As noted earlier, the gas carrying capacity of the pharmaceutical composition is proportional to its lipid content. Accordingly, pharmaceutical composition with high lipid content (e.g., 30-50% v/v) is used when a high Xenon dose is needed. In another embodiment, the pharmaceutical composition is saturated with a mixture of xenon and oxygen with the percentage loaded with xenon or argon from 10 to 80% (v/v). In one embodiment, the pharmaceutical composition is saturated with a mixture of xenon/argon and oxygen at a xenon/argon:oxygen ratio of 50:50, 60:40, 70:30, 75:25, or 80:20 (v/v). In yet another embodiment, the pharmaceutical composition is a mixture of a first pharmaceutical composition saturated with xenon or argon and a second pharmaceutical composition saturated with oxygen. In yet another embodiment, xenon or argon is used in conjunction with another volatile anesthetic, such as sevoflurane.

The treatable neuronal injuries involving NMDA receptors, include but are not limited to, ischemic stroke, intracranial bleeding due to trauma, or anoxic brain injury caused by blood loss or other forms of shock or seizure disorder, and encephalitis.

In one embodiment, neuronal injuries are injuries mediated by methyl-D-aspartate (NMDA)-type glutamate receptors. In another embodiment, the neuronal injuries are injuries caused by oxygen deprivation in the brain.

In certain embodiments the xenon, argon, $Xe/O_2$ or $Ar/O_2$-carrying pharmaceutical composition is infused at a rate of 20 to 100,000 ml/hour, 500 to 100,000 ml/hour, or 5000 to 60,000 ml/hour. The infusion may last for a period of several minutes to several weeks, depending on the condition and specific needs of the patient. In certain embodiments, the xenon, argon, $Xe/O_2$ or $Ar/O_2$-carrying pharmaceutical composition is infused for a period of 3 to 600 minutes, 5-300 minutes, 10-120 minutes, 10 to 24 hours, or 1 to 7 days.

In another embodiment, the xenon-carrying pharmaceutical composition also carries a desired amount of carbon monoxide to prevent the development of pathologic conditions such as ischemia reperfusion injury.

In another embodiment, the xenon-carrying pharmaceutical composition also carries a desired amount of hydrogen sulfide to regulate brain perfusion and promote organ survival.

In another embodiment, the xenon-carrying pharmaceutical composition is used in combination with hypothemia (32° C.-34° C.) for treating neuronal injuries. Xenon may similarly be used in cardiac disease given its utility in treating heart failure (Baumert J H, Falter F, Eletr D, Hecker K E, Reyle-Hahn M, Rossaint R. Xenon anaesthesia may preserve cardiovascular function in patients with heart failure. Acta Anaesthesiol Scand. 2005 July; 49(6):743-9

In one embodiment, the xenon/argon treatment is given within 72 hours of neuronal injury or brain ischemia.

In another embodiment, the xenon/argon treatment is given within 24 hours of neuronal injury or brain ischemia.

In another embodiment, the xenon/argon treatment is given within 8 hours of neuronal injury or brain ischemia.

In another embodiment, the xenon/argon treatment is given within 4 hours of neuronal injury or brain ischemia.

In another embodiment, the xenon/argon treatment is given within 2 hours of neuronal injury or brain ischemia.

Treatment of the Hypotension of Septic Shock with the Pharmaceutical Composition of the Present Invention Another aspect of the present invention relates to a method for treating septic shock in a subject with pharmaceutical composition to absorb endogenously produced nitric oxide. Septic shock, or sepsis, is a medical condition in which acute inflammation, low blood pressure, and blood clotting cause a dangerous decrease in the delivery of blood to the organs. Because of the failure of oxygen delivery to the microciculation and the inability to utilize oxygen, once delivered to tissues the patient's organs start to fail, one after the other. Currently, only supportive treatment is available. Nitric oxide plays a prominent role in the pathophysiology of both hemorrhagic and septic shock. Excess nitric oxide release from endothelial cells cause relaxation of arterial smooth muscle cells, loss of vascular tone and hypotension resulting in the inability to perfuse the microcirculation. In addition, nitric oxide can interact with reactive oxygen species and form toxic products such as peroxynitrite. In such cases it would beneficial to remove excess nitric oxide. Therefore, in one embodiment, the method comprises administering into said subject, an effective amount of the pharmaceutical composition for a desired period of time to absorb or remove endogenously released nitric oxide from the circulation system. The nitric oxide-absorbing pharmaceutical composition can be administered intravenously or intra-arterially at a rate of about 20 ml/hour to about 15,000 ml/min, preferably at a rate of 4000 ml/minute.

Treatment of Vasoconstriction and/or Hypertension with Nitric Oxide-Carrying Pharmaceutical Composition of the Present Invention Some diseases such as Raynaud's disease occur because of increased vascular resistance. Other examples are Prinzmetal's angina, cerebral vasospasm and atherosclerosis. In this case loading the pharmaceutical composition with nitric oxide would relieve the vasoconstriction. Also in sickle cell crisis a combination of micelles loaded with nitric oxide and oxygen would be useful with the nitric oxide loaded micelles opening constricted small vessels while oxygen loaded cells delivered oxygen to ischemic tissues. Oxygen free radicals would be scavenged by the antioxidant moieties within the emulsion. In all embodiments the nitric-oxide carrying pharmaceutical composition also carries a desired amount oxygen or other gases depending upon the physiological need. In another embodiment, the nitric-oxide carrying pharmaceutical composition also carries a desired amount of carbon monoxide to prevent the development of pathologic conditions such as ischemia reperfusion injury.

In another embodiment, the nitric-oxide carrying pharmaceutical composition also carries a desired amount of hydrogen sulfide to promote perfusion of the brain and to modulate apoptosis.

Preservation of Organs

Another aspect of the present invention relates to a method of preserving the biological integrity of organs of a mammalian donor organism using the pharmaceutical composition described. In one embodiment, the subject organ is chilled and the pharmaceutical composition is perfused into the subject organ using a pumped circulating device such as a centrifugal pump, roller pump, peristaltic pump or other known and available circulatory pump. The circulating device is connected to the subject organ via cannulae inserted surgically into appropriate veins and arteries. When the pharmaceutical composition is administered to a chilled subject organ, it is generally administered via an arterial cannula and removed from the subject via a venous cannula and discarded or stored. In another embodiment, the pharmaceutical composition is perfused at a temperature in the room temperature range (15° C. to 25° C.). In another embodiment, the pharmaceutical composition is perfused at a temperature in the sub-body temperature range (25° C. to 34° C.). In another embodiment, the pharmaceutical composition is perfused at a temperature in the body temperature range (34° C. to 39° C.).

When used for organ perfusion during an organ transplantation, the pharmaceutical composition may be administered over a period of hours. In certain embodiments, the pharmaceutical composition comprises chia bean oil for its immunosuppressive effect.

Diagnosis

The pharmaceutical composition of the present invention may also be used as a diagnostic tool. Because of its hydrophobic properties, the pharmaceutical composition is capable of absorbing lipophilic moieties that are produced in various disease states. Analysis of the pharmaceutical composition after it has circulated through the blood stream can reveal the presence of diseases that release such moieties into the bloodstream. An example is the production of increased carbon monoxide and nitric oxide in septic shock or other diseases that involve the induction of heme oxygenase that leads to increased production endogenous carbon monoxide.

EXAMPLES

The following example is put forth so as to provide those of ordinary skill in the art with a complete disclosure and description of how to carry out the method of the present invention and is not intended to limit the scope of the invention. Efforts have been made to ensure accuracy with respect to numbers used (e.g., amounts, temperature, etc.), but some experimental error and deviation should be accounted for. Unless indicated otherwise, parts are parts by weight, molecular weight is weight average molecular weight, temperature is in degrees Centigrade, and pressure is at or near atmospheric.

Example 1

Methods and Materials

Lipid Emulsions Prepared by Sonication:

Lipid emulsion of various concentrations was prepared by mixing 1-3 grams of soybean oil, 0.12 grams of soy lecithin, and 0.24 grams of glycerol and water to make the volume up to 10 ml. This mixture was put into a 15 ml vial and emulsified in an ice bath using an ultrasound cell disruptor.

Lipid Emulsions Prepared by Homogenization and Microfluidization:

An emulsion consisting of soybean oil (SIGMA, St. Louis) was prepared. The composition was composed of between 20%-50% w/v soybean oil, de-ionized water, varying amounts of an emulsifying agent (either phosphotidylcholine (Avanti Polar Lipids, Alabaster, Ala.) or egg yolk phospholipids (Sigma-Aldrich, St. Louis, Mo.), and with or without 5% human serum albumin (Sigma-Aldrich, St. Louis, Mo.). The albumin was added after the formation of the micelles. Some samples also contained 154 mM NaCl. The mixture was homogenized for five minutes with a Silverson® high-shear rotor/stator homogenizer. A M-110T® microfluidizer (Microfluidics, Newton, Mass.) was used for final homogenization of the coarse emulsion prepared by the Silverson homogenizer.

Commercially Obtained Lipid Emulsions:

20% Intralipid® (marketed and sold by Baxter International Inc., Deerfield, Ill.) was used as a model lipid emulsion. It is composed of 20% soy bean oil, 1.2% egg yolk phospholipids 2.25% glycerin, water and sodium hydroxide to adjust the pH to 8. Another model lipid emulsion obtained commercially is Liposyn® III 20% sold by Hospira in Lake Forest, Ill. This emulsion consists of 20% soybean oil, 1.2% egg phospholipids, 2.5% glycerin, water and NaOH to adjust the pH to 8.3.

Determination of Oxygen Content of Emulsions Using Mass Spectroscopy:

The technique developed in Dr. Juan Rodriguez' laboratory was employed (Cornelius J, Tran T, Turner N, Piazza A, Mills L, Slack R, Hauser S, Alexander J S, Grisham M B, Feelisch M, Rodriguez J. "Isotope tracing enhancement of chemiluminescence assays for nitric oxide research" Biol. Chem. February; 390(2):181-9 (2009)). Some samples (1 ml each) were left open to air in 2.0 ml tubes for 30 minutes prior to dissolved gas analysis. In other experiments the emulsion was placed into a 15 ml tube. The headspace was filled with the gas under study and the gas was allowed to enter the emulsion by equilibration over 60 minutes with the tube on its side to increase the gas emulsion interaction. 50 µL drawn from each of these fluids were injected into a Sievers purge vessel at 37° C. containing 36 ml of a mildly acidic solution consisting of 32 ml of 1M HCL and 4 ml of 0.5M ascorbic acid. The solution was continuously purged with high purity helium to transport any oxygen released from the samples to a mass spectrometer (HP 5975) for direct gas analysis. Signals generated at m/z=32 upon injection of RL and lipid emulsion samples were integrated using Peakfit and compared to those obtained with distilled water.

Animals and Animal Procedures:

Male and female mice weighing 27-47 grams were utilized. The strains were either CD-1 or NFR2. All comparisons utilized the same strain. Mice were anesthetized using ketamine/xylazine anesthesia administered subcutaneously. In order to prevent the skewing of data due to the cardiodepressant effects of the anesthetic agent, the experiment was aborted and the mouse euthanized in the rare instance when more anesthetic was required than the calculated dose. Once it was clear that the mouse was well-anesthetized, the carotid artery was cannulated. As much blood as possible was removed in three minutes. This resulted in the loss of 55% of blood volume and 100% lethality without any infusion. Immediately after blood removal infusions were administered over two minutes.

Pharmaceutical composition, resuscitation fluid (Ringer's lactate) or shed blood was administered at a volume equal to the amount of blood that had been removed. Blood pressure was measured at the carotid artery using a BP-2 monitor made by Columbus Instruments (Columbus, Ohio). This monitor measures the blood pressure as a voltage. A standard curve was prepared. Measured voltages were converted to blood pressure (BP) using the following formula:

$$BP=[Voltage-0.1006]/0.0107$$

No warming measures were applied to the mice. No measures were taken to support respiration.

Rat Model of Hemorrhagic Shock

Experiments using rats were approved by the University of Tennessee Health Science Center Animal Care and Use Committee. Sprague-Dawley rats weighing between 200 and 300 g were purchased with the carotid artery and ipsilateral jugular vein pre-cannulated. The rats were given ketamine/xylazine anesthesia subcutaneously. After the effectiveness of the anesthetic was assured the carotid cannula was connected with a blood pressure monitor. The rats were bled to a mean blood pressure of 40 mmHg and maintained at that level for 45 minutes by the removal or infusion of shed blood as needed. At the end of the 45 minute period of shock the test pharmaceutical composition was infused in a volume equal to the amount of blood removed. The blood pressure was recorded for 45 minutes after resuscitation after which surviving rats were euthanized by exsanguination.

Statistical Analysis:

Data were analyzed using the two-tailed, Student's unpaired t test.

Example 2

Oxygen and Nitric Oxide Content of the Pharmaceutical Composition of the Present Invention Intralipid® 20% I.V. Fat Emulsion (marketed and sold by Baxter International Inc., Deerfield, Ill.) was used as a sample pharmaceutical composition (LM). The composition of Intralipid® is 20% soybean oil, 1.2% egg yolk phospholipids, 2.25% glycerin, water and sodium hydroxide to adjust the pH to 8. Oxygen content in the samples was measured using mass spectrometry. As shown in Table I, the oxygen content of LM was nearly twice that of Ringer's lactate (RL), a standard resuscitation fluid infused when a large amount of blood is lost. The oxygen content of water was assigned the value of 1. The oxygen content of RL was slightly less than that of water. As shown in Table 2, the oxygen content of the LM was increased five-fold by bubbling oxygen through it for approximately 1 minute. After oxygen loading, the oxygen content of LM compared favorably to that of blood with the minimum acceptable hemoglobin level (i.e., 7.0 g/dl).

TABLE 1

Oxygen content of Ringer's lactate and Intralipid ® 20%.
Each mean is the result of 3 samples.

|  | Ringer's lactate | Intralipid ® 20% |
|---|---|---|
| Oxygen Content* | 0.91 ± 0.11* | 1.78 ± 0.09* |

*the oxygen content is expressed as the amount relative to the oxygen content in water.

TABLE 2

Oxygen solubility in various liquids at 1 atm
Oxygen Content at 25° C. and Sea level Pressure

| Blood (hemoglobin of 7.0) | 72.8 mg/L |
|---|---|
| Water | 8.3 mg/L+ |
| LM (20%) | 15.1 mg/L |
| LM (20% after oxygen perfusion) | 75.5 mg/L |

+Obtained from "The Engineering Toolbox" *Oxygen Solubility in Fresh and Sea water* at http://www.engineeringtoolbox.com/oxygen-solubility-water-d_841.html.

These data show that LM may be loaded with sufficient oxygen to provide for aerobic metabolism. This point is further underscored by the fact that only 30% of the oxygen bound to hemoglobin is used under normal circumstances. In extreme stress such as severe hemorrhagic shock 60% might be offloaded from hemoglobin. In contrast all of the oxygen dissolved in LM should be available given the fact that oxygen is released 3 times faster from LM than from hemoglobin. The published release time for hemoglobin is 17.5 msec while the off time measured when we purged oxygen from LM was less than 5 msec.

Figure 2:
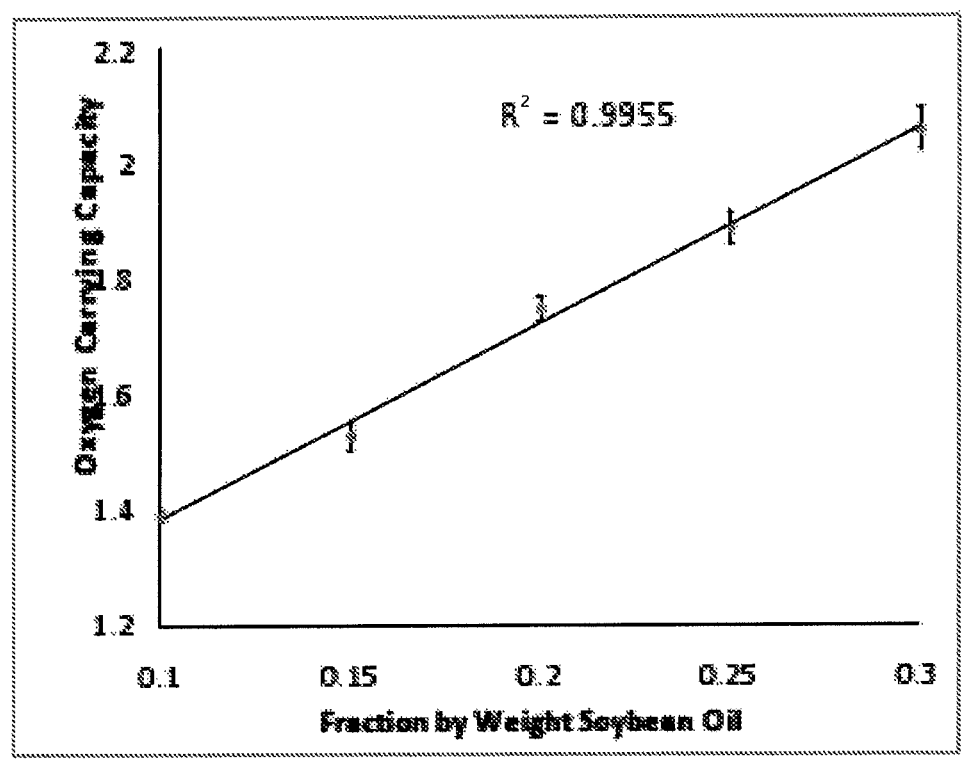
FIG. 2 is a graph showing the linear relationship between micelle concentration and oxygen content. Oxygen content was measured using mass spectroscopy. The Y axis, designated "Carrying Capacity" is the ratio of the oxygen content of the emulsion over that of water in which both fluids were exposed to the same conditions. The X axis is the of the emulsion comprised of micelles. The emulsion was prepared by sonication of a mixture comprised of 1-3 grams of purified soybean oil, 0.1 grams of soy lecithin and 0.24 grams of glycerol and water to bring the mixture to a volume of 10 ml. Each point is the mean of 5 samples.

FIG. 2 shows the linear dependence of emulsion oxygen content on the concentration of lipid micelles. Micelles were prepared by sonicating a mixture of 1-3 grams of soybean oil, 0.12 gram of soybean lecithin and 0.12 gram of glycerol and water to make a volume of 10 ml. The mixture was put into a 15 ml tube and emulsified in an ice bath using an ultrasound disruptor. Each point is the mean of 2-3 experiments. The Y axis is the oxygen content of the emulsion relative to water. The X axis is the soybean oil concentration of the emulsion.

Example 3

Nitric Oxide Uptake of the Pharmaceutical Composition of the Present Invention

In another set of experiments we measured the uptake of nitric oxide by a commercially available 20% soybean oil emulsion, Liposyn III 20%. This emulsion contains 20% soybean oil, 1.2% egg phospholipids and 2.5% glycerin in water. Using NaOH pH was adjusted to 8.3. Oxygen was added by equilibration in which 200 µl of the emulsion was placed into a 15 ml vial. 100 ppm nitric oxide in helium was used to purge the headspace for two minutes taking care not to bubble the fluid. For sixty minutes the sample was allowed to reach gas-liquid equilibrium with the tube placed on its side to maximize gas-emulsion contact. The results are shown in table 3 below.

TABLE 3

NO Content of a 20% Soybean Oil Emulsion (Liposyn III 20%) and Water in moles/liter

| Emulsion | Water |
|---|---|
| 3.03 | 1.52 |
| 2.42 | 1.63 |
| 3.81 | 1.72 |
| 3.30 | 1.69 |
| 2.50 | 2.29 |
| Mean 3.01 | 1.77 |
| S.E 0.26 | 0.14 |

Example 4

The Effect of the Pharmaceutical Composition of the Present Invention in Restoring Arterial Pressure in Mice with Severe Hemorrhagic Shock The effect of the pharmaceutical composition (LM) in Example 2 on blood pressure was determined in mice. Mice were anesthetized and a cannula was placed into the carotid artery. All the blood that could be removed was removed via the carotid artery. After the blood was removed a volume of either RL or LM was given equal to the amount of blood removed. 6 mice were in the LM group and 6 mice were in the RL group. The observation period was one hour. Two of the mice given RL died within ten minutes. All mice given LM lived through the entire hour observation period and until euthanized at 1-4 hours. Animals were euthanized whenever they began to awaken from the anesthesia or at the end of the observation period to prevent suffering.

Figure 3:
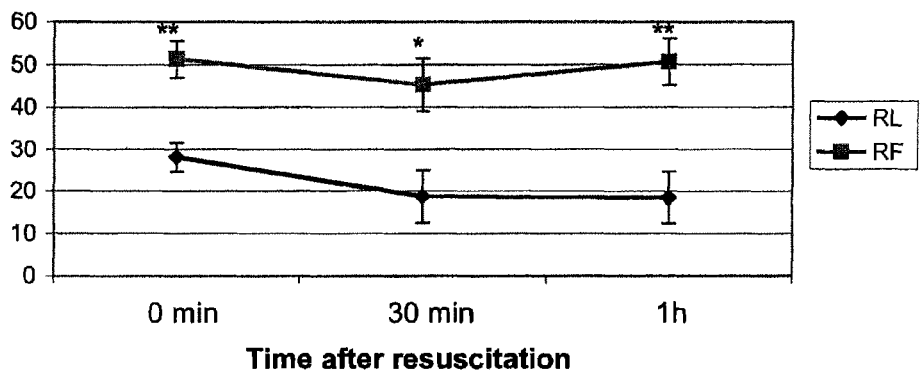
FIG. 3 is a diagram showing systolic blood pressure in mice treated with different pharmaceutical compositions after severe hemorrhagic shock. LM is a commercially available model 20% soybean oil emulsion (Intralipid) alone. RL is Ringer's (L) lactate. The mean blood pressure immediately before infusion across all experiments of [resuscitation] fluid was 4.6+/−1.2 mmHg. The systolic pressure immediately before infusion of the fluid is subtracted out. Each point is the mean of 6-7 mice. **=p<0.01, *=p<0.05 for both the systolic and diastolic pressures of FIGS. 3 and 4, using a two tailed unpaired Student's t test.
Figure 4:
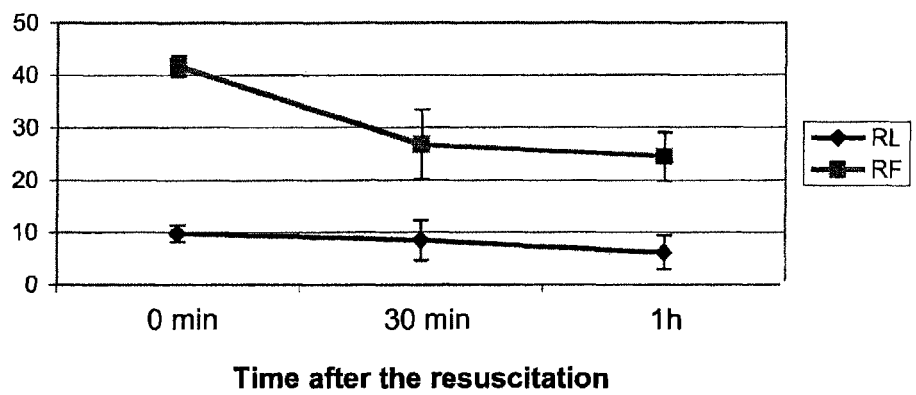
FIG. 4 is a diagram showing diastolic blood pressure in mice treated with different pharmaceutical compositions after severe hemorrhagic shock. LM is a commercially available model 20% soybean oil emulsion (Intralipid) alone. RL is Ringer's (L) lactate. The mean blood pressure immediately before infusion across all experiments was 4.6+/−1.2 mmHg. The diastolic pressure immediately before infusion of the fluid is subtracted out. Each point is the mean of 6-7 mice. P values are as with the corresponding systolic pressure in FIG. 3.

FIGS. 3 and 4 show the difference between the systolic blood pressure (FIG. 3) and diastolic blood pressure (FIG. 4) after hemorrhage and after infusion of RL or LM at time=0, 30 and 60 minutes. The Y axis represents the blood pressure attained after infusion minus the blood pressure after hemorrhage in mm of Hg. The X axis shows the specific time after the infusion. All data were analyzed for statistical significance using an unpaired two tailed t test. These graphs show that LM raised the blood pressure higher than RL (p<0.01).

Figure 5:
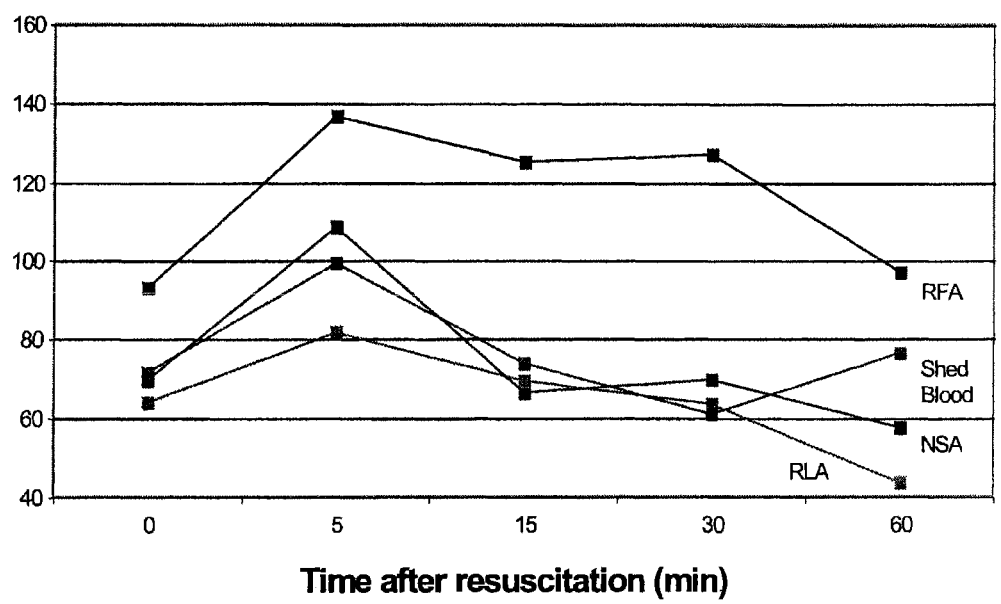
FIG. 5 is a diagram showing the mean blood pressure after infusion as a percentage of the mean pre-hemorrhage blood pressure in mice treated with albumin-containing [resuscitation] fluids and mice treated with shed blood after severe hemorrhagic shock. The zero time point is the first pressure after initial infusion. There was no significant difference between the pre-infusion pressures of any of the groups. Each point is the mean of 6-7 mice. VS is the combination of 5% albumin with 20% Intralipid. NSA is 5% albumin in 154 mM NaCL. RLA is 5% albumin in Ringer's lactate. VS is significantly higher (p<0.05) than shed blood at 5, 15 and 30 minutes using a two tailed, unpaired Student's test.

In another experiment, a pharmaceutical composition containing Intralipid® 20% and 5% (w/v) albumin was prepared by dissolving albumin (Sigma Aldrich, 99% pure, fatty acid free, essentially globulin free, catalog number A3782-5G) in Intralipid® 20% to a final concentration of 50 mg/ml. The new pharmaceutical composition with albumin (VS) was tested using the experimental procedure described above. Albumin dissolved in normal saline (NSA) and Ringer's lactate (RLA) at 50 mg/ml, as well as the shed blood (i.e., the blood that had been removed from the mice), were used as controls. In FIG. 5, the Y axis shows the mean blood pressure (expressed as percentage of mean pre-hemorrhage blood pressure) achieved by infusion of the various fluids. The X axis shows specific times after the infusion. The data show that VS is superior even to shed blood in maintaining blood pressure. Similar results were also obtained for the diastolic blood pressure (not shown). For each time point, an average of 6-7 mice is plotted. Differences between shed blood and VS was statistically significant (P<0.05) at 5, 15 and 30 minutes.

Example 5

The Effect of the Pharmaceutical Composition of the Present Invention in Restoring Arterial Pressure in Rats with Severe Hemorrhagic Shock In another experiment anesthetized rats were bled to a mean pressure of 40 that was maintained for 45 minutes using shed blood. At the end of this period a test fluid was given within 2 minutes. The test fluids were the (1) emulsion containing 20% Intralipid mixed with 5% albumin NaCl 102 mM, Na(L) lactate 28 mM, KCL 4 mM, (2) Ringer's lactate, (3) Hextend and (4) shed blood. The results are shown in Table 4.

TABLE 4

Effect of the pharmaceutical composition in restoring arterial pressure in rats with severe hemorrhagic shock

|  | Emulsion | Hextend | Ringer's Lactate | Blood |
| --- | --- | --- | --- | --- |
| Number of rats | 6 | 2 | 2 | 2 |
| Avg survival time (min) | 35.8 +/− 6.7 | 10.74 | 18.25 | 35.75 |
| Avg mean arterial pressure | 64.2 +/− 2.4 | 38.3 | 34.2 | 64.7 |

Hematoxylin and eosin histopathological examination of the lung, liver, kidneys, spleen heart and intestine was carried out. No harmful effect of the emulsion was found.

These experimental results are consistent with the fact that the lipid micelles in the pharmaceutical composition are capable of exerting an osmotic force and absorbing mediators of vascular patency, such as prostaglandins, nitric oxide, leukotrienes, and hromboxane.

Example 6

The Effect of Amino Acid-Containing Pharmaceutical Composition in Restoring Arterial Pressure in Rats with Severe Hemorrhagic Shock In another experiment, hemorrhagic shock was induced in mice as described in Example 4. The mice were then resuscitated with a control emulsion containing 20% Intralipid, 102 mM NaCl, 28 mM Na(L) lactate, 4 mM KCL, or an test emulsion containing the control emulsion and 1 mM histidine or tyrosine or phenylalanine or cysteine. Table 4 shows the effect of the pharmaceutical composition in restoring arterial pressure in mice with hemorrhagic shock.

TABLE 5

Effect of the pharmaceutical composition in restoring arterial pressure in mice with hemorrhagic shock.

|  | # mice | Pre bleed | Shock | Post infusion - pressure in shock |
| --- | --- | --- | --- | --- |
| IL alone | 4 | 105.0 +/− 3.6 | 22.8 +/− 2.8 | 32.3 +/− 6.8 |
|  |  | 79.0 +/− 2.3 | 14.5 +/− 2.4 | 8.3 +/− 3.1 |
| IL + Histidine | 2 | 112.0 +/− 13.0 | 16.04 +/− 0 | 63.0 +/− 4.0 |
|  |  | 83.0 +/− 7.0 | 10.5 +/− 0.5 | 43.0 +/− 0 |
| IL + Tyrosine | 2 | 134 +/− 18.0 | 24.0 +/− 1.0 | 68.0 +/− 3.0 |
|  |  | 83.0 +/− 16 | 15.0 +/− 1.0 | 56.5 +/− 2.5 |
| IL + Phenylalanine | 2 | 106.5 +/− 21.5 | 19.5 +/− 2.5 | 55.5 +/− 2.5 |
|  |  | 70.5 +/− 14.5 | 13.5 +/− 0.5 | 42.0 +/− 6.0 |
| IL + cysteine | 2 | 156.5 +/− 37.5 | 25.0 +/− 0 | 58.5 +/− 3.5 |
|  |  | 99.0 +/− 14.0 | 16.0 +/− 3.0 | 45.0 +/− 5.0 |

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

What is claimed is:

1. A pharmaceutical composition comprising:
   a lipid component;
   an amphiphilic emulsifier; and
   a polar liquid carrier,
   wherein the lipid component and the amphiphilic emulsifier form free-moving lipid-carrying micelles (LMs) or liposomes in the polar liquid carrier, wherein the pharmaceutical composition is free of hemoglobin and fluorocarbon, and wherein the pharmaceutical composition further comprises an effective amount of oxygen for enhancement of aerobic metabolism.

2. The pharmaceutical composition of claim 1, wherein said LMs or liposomes have an average diameter of 300 nm or smaller.

3. The pharmaceutical composition of claim 1, wherein said LMs or liposomes have an average diameter of 100 nm or smaller.

4. The pharmaceutical composition of claim 1, wherein said LMs or liposomes have an average diameter of 30 nm or smaller.

5. The pharmaceutical composition of claim 1, further comprising an amino acid at a final concentration of 0.2-50 mM.

6. The pharmaceutical composition of claim 1, further comprising glycerol or mannitol in an amount of 2-5% (w/v).

7. The pharmaceutical composition of claim 1, further comprising glycerol or mannitol in an amount of about 2.25% (w/v).

8. The pharmaceutical composition of claim 1, further comprising albumin in an amount of 3-7% (w/v).

9. The pharmaceutical composition of claim 1, further comprising albumin in an amount of about 5% (w/v).

10. The pharmaceutical composition of claim 1, wherein said amphiphilic emulsifier is egg yolk phospholipids or α-phosphatidylcholine in an amount of 1%-5% (w/v).

11. The pharmaceutical composition of claim 10, wherein said amphiphilic emulsifier is egg yolk phospholipids or α-phosphatidylcholine in an amount of about 2% (w/v).

12. The pharmaceutical composition of claim 1, wherein said lipid component is selected from the group consisting of soybean oil, chia bean oil, pumpkin oil, flaxseed oil, fish oil and algae oil in an amount of 10%-70% (w/v) of said pharmaceutical composition.

13. The pharmaceutical composition of claim 12, wherein said lipid component is selected from the group consisting of soybean oil, chia bean oil and algae oil in an amount of about 35% (w/v) of said pharmaceutical composition.

14. The pharmaceutical composition of claim 1, wherein said composition is free of calcium, magnesium and potassium.

15. The pharmaceutical composition of claim 1, wherein said composition is free of aluminium.

16. The pharmaceutical composition of claim 1, wherein said LMs or liposomes have an average diameter of 2-300 nm.

17. The pharmaceutical composition of claim 1, further comprising an amino acid at a final concentration of 0.1 fM-200 mM.

18. The pharmaceutical composition of claim 1, further comprising an amino acid at a final concentration of 0.1 fM-10 mM.

19. The pharmaceutical composition of claim 1, further comprising an amino acid at a final concentration of 0.01 mM-200 mM.

20. The pharmaceutical composition of claim 1, further comprising an amino acid at a final concentration of 10 nM-10 μM.

21. The pharmaceutical composition of claim 1, further comprising effective amounts of oxygen and nitric oxide for regulation of vascular function and cellular metabolism.

22. The pharmaceutical composition of claim 1, further comprising erythrocyte ghosts that traps said lipid component.

23. The pharmaceutical composition of claim 1, further comprising β-endorphin at a final concentration of 0.01-100 nM.

24. The pharmaceutical composition of claim 1, further comprising 0.1 fM-10 mM histidine, cysteine, or an oligopeptide containing histidine or glycylglycine.

25. The pharmaceutical composition of claim 1, further comprising 0.01-0.2 M histidine.

26. The pharmaceutical composition of claim 1, wherein said lipid carrying micelles or liposomes have an average diameter of 90-120 nm.

27. The pharmaceutical composition of claim 1, wherein said lipid carrying micelles or liposomes have an average diameter of 90-100 nm.

28. The pharmaceutical composition of claim 1, wherein said lipid carrying micelles or liposomes have an average diameter of 100-110 nm.

29. The pharmaceutical composition of claim 1, wherein said lipid carrying micelles or liposomes have an average diameter of 110-120 nm.

30. The pharmaceutical composition of claim 1, further comprising one or more oncotic agents.

31. The pharmaceutical composition of claim 1, further comprising one or more immunomodulatory agents.

32. The pharmaceutical composition of claim 1, further comprising one or more anti-inflammatory agents.

33. The pharmaceutical composition of claim 1, further comprising one or more coagulation enhancers.

34. The pharmaceutical composition of claim 1, further comprising one or more additives selected from the group consisting of antioxidants, antibiotics, anti-fungal agents, vitamins, amino acids, vessel expanders, surfactants, antibodies and mediators of vascular potency.

* * * * *